(12) United States Patent
Honma et al.

(10) Patent No.: US 7,135,540 B2
(45) Date of Patent: Nov. 14, 2006

(54) POLYHYDROXYALKANOATE COPOLYMER INCLUDING UNIT HAVING BROMO GROUP IN SIDE CHAIN AND METHOD FOR PRODUCING THE SAME

(75) Inventors: Tsutomu Honma, Kanagawa (JP); Shinya Kozaki, Tokyo (JP); Takeshi Imamura, Kanagawa (JP); Takashi Kenmoku, Kanagawa (JP); Tatsuki Fukui, Kanagawa (JP); Etsuko Sugawa, Kanagawa (JP); Tetsuya Yano, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 497 days.

(21) Appl. No.: 10/359,600

(22) Filed: Feb. 7, 2003

(65) Prior Publication Data

US 2003/0194789 A1    Oct. 16, 2003

(30) Foreign Application Priority Data

| Feb. 15, 2002 | (JP) | ............................. 2002-039255 |
| Oct. 24, 2002 | (JP) | ............................. 2002-310268 |
| Dec. 13, 2002 | (JP) | ............................. 2002-362594 |

(51) Int. Cl.
  *C08G 63/02* (2006.01)
(52) U.S. Cl. ........................ 528/272; 435/135; 528/179; 528/271
(58) Field of Classification Search ................. 435/135; 528/179, 271, 272
See application file for complete search history.

(56) References Cited

U.S. PATENT DOCUMENTS

| | | | | |
|---|---|---|---|---|
| 4,393,167 A | 7/1983 | Holmes et al. | ................ | 525/64 |
| 4,477,654 A | 10/1984 | Holmes et al. | ............... | 528/361 |
| 4,876,331 A | 10/1989 | Doi | ............................ | 528/361 |
| 5,135,859 A | 8/1992 | Witholt et al. | .............. | 435/135 |
| 5,191,016 A | 3/1993 | Yalpani | ..................... | 525/54.2 |
| 5,200,332 A | 4/1993 | Yamane et al. | ............. | 435/135 |
| 5,292,860 A | 3/1994 | Shiotani et al. | ............. | 528/361 |
| 5,334,698 A | 8/1994 | Witholt et al. | .............. | 528/354 |
| 5,811,272 A | 9/1998 | Snell et al. | .................. | 435/135 |
| 6,156,852 A | 12/2000 | Asrar et al. | .................. | 525/450 |
| 6,492,147 B1 * | 12/2002 | Imamura et al. | ............ | 435/135 |
| 6,521,429 B1 * | 2/2003 | Honma et al. | ............... | 435/135 |
| 6,586,562 B1 | 7/2003 | Honma et al. | ............... | 528/361 |
| 6,635,782 B1 | 10/2003 | Honma et al. | ................ | 560/53 |
| 6,645,743 B1 | 11/2003 | Honma et al. | ............... | 435/146 |
| 6,649,380 B1 | 11/2003 | Yano et al. | .................. | 435/135 |
| 6,649,381 B1 | 11/2003 | Honma et al. | ............... | 435/135 |
| 2001/0029039 A1 * | 10/2001 | Honma et al. | ............... | 435/135 |
| 2002/0052444 A1 | 5/2002 | Imamura et al. | ............ | 525/107 |
| 2002/0160467 A1 * | 10/2002 | Honma et al. | ............... | 435/135 |
| 2003/0013841 A1 | 1/2003 | Imamura et al. | ............ | 528/271 |
| 2003/0096182 A1 | 5/2003 | Yano et al. | ................. | 430/108.5 |
| 2003/0096384 A1 | 5/2003 | Kenmoku et al. | .......... | 435/135 |
| 2003/0104300 A1 | 6/2003 | Kenmoku et al. | ...... | 430/108.22 |
| 2003/0113368 A1 | 6/2003 | Nomoto et al. | ............. | 424/450 |
| 2004/0067576 A1 | 4/2004 | Honma et al. | ......... | 435/252.34 |

FOREIGN PATENT DOCUMENTS

| | | |
|---|---|---|
| CN | 1321695 A | 11/2001 |
| EP | 0 416 624 A2 | 3/1991 |
| EP | 1 113 033 A2 | 7/2001 |
| EP | 1 130 042 A2 | 9/2001 |
| EP | 1 130 043 A2 | 9/2001 |
| EP | 1 188 782 A2 | 3/2002 |
| EP | 1 236 752 A2 | 9/2002 |
| EP | 1 236 754 A2 | 9/2002 |
| EP | 1 236 755 A2 | 9/2002 |
| EP | 1 245 605 A2 | 10/2002 |
| EP | 1 253 161 A2 | 10/2002 |
| EP | 1 253 162 A2 | 10/2002 |
| EP | 1 262 508 A2 | 12/2002 |
| EP | 1 275 727 A2 | 1/2003 |
| JP | 59-190945 | 10/1984 |
| JP | 63-226291 | 9/1988 |
| JP | 5-7492 | 1/1993 |
| JP | 5-93049 | 4/1993 |
| JP | 6-15604 | 3/1994 |
| JP | 7-14352 | 2/1995 |
| JP | 7-265065 | 10/1995 |
| JP | 8-19227 | 2/1996 |
| JP | 2642937 | 5/1997 |
| JP | 9-191893 | 7/1997 |
| JP | 2000-72865 | * 3/2000 |
| JP | 2001-178484 | 7/2001 |
| JP | 2001-288256 | * 10/2001 |
| WO | 97/07153 A1 | 2/1997 |

(Continued)

OTHER PUBLICATIONS

K. Fritzsche et al., "An Unusual Bacterial Polyester With a Phenyl Pendant Group," 191 *Makromol. Chem.* 1957-1965 (1990).*

(Continued)

*Primary Examiner*—Terressa Boykin
(74) *Attorney, Agent, or Firm*—Fitzpatrick, Cella, Harper & Scinto

(57) ABSTRACT

The invention provides a polyhydroxyalkanoate having a bromo group in a unit and being thermally stable and capable of arbitrarily controlling physical properties, and a producing method thereof. According to the invention, there are provided a polyhydroxyalkanoate copolymer including a 3-hydroxy-ω-bromoalkanoic acid unit represented by a formula —[OCH((CH$_2$)$_n$Br)CH$_2$C(O)]— (n=1 to 8) (1) and a unit represented by a formula —[OCH((CH$_2$)$_m$R)CH$_2$C(O)]— (2) within a same molecule, and a method for producing a polyhydroxyalkanoate copolymer by microorganisms, utilizing a ω-bromoalkanoic acid represented by a formula Br(CH$_2$)$_p$CH$_2$CH$_2$COOH (p=1 to 8) (20) and a compound represented by a formula R(CH$_2$)$_q$CH$_2$CH$_2$COOH (21) as raw materials.

16 Claims, 8 Drawing Sheets

FOREIGN PATENT DOCUMENTS

WO   02/16627 A2   2/2002

OTHER PUBLICATIONS

Y.B. Kim et al., "Preparation and Characterization of Poly(β-hydroxyalkanoates) Obtain d from *Pseudomonas oleovorans* Grown with Mixtures of 5-Phenylvaleric Acid and n-Alkanoic Acids," 24 *Macromol.* 5256-5260 (1991).*

Joanne M. Curley et al., "Production of Poly(3-hydroxyalkanoates) Containing Aromatic Substituents by *Pseudomonas oleovorans*," 29 *Macromol.* 1762-1766 (1996).*

Suzette M. Aróstegui et al., "Bacterial Polyesters Produced by *Pseudomonas oleovorans* Containing Nitrophenyl Groups," 32 *Macromol.* 2889-2895 (1999).*

Helmut Ritter et al., "Bacterial Production of Polyesters Bearing Phenoxy Groups in the Sid Chain, 1 Poly(3-hydroxy-5-phenoxypentanoate-co-3-hydroxy-9-phenoxy-nonanoate) from *Pseudomonas oleovorans*," 195 *Macromol. Chem. Phys.* 1665-1672 (1994).

Ohyoung Kim et al., "Bioengineering of Poly(β-hydroxyalkanoates) for Advanced Material Applications: Incorporation of Cyano and Nitrophenoxy Side Chain Substituents," 41 (Supp. 1) *Can. J. Microbiol.* 32-43 (1995).

Richard A. Gross et al., "Cyanophenoxy-Containing Microbal Polyesters: Structural Analysis, Thermal Properties, Second Harmonic Generation and In-Vivo Biodegradability," 39 *Polymer International* 205-213 (1996).

Young B. Kim et al., "Poly(β-hydroxyalkanoate) Copolymers Containing Brominated Repeating Units Produced by *Pseudomonas oleovorans*," 25 *Macromol.* 1852-1857 (1992).

Marieta Constantin et al., "Chemical Modification of Poly(hydroxyalkanoates). Copolym rs Bearing Pendant Sugars," 20 *Macromol. Rapid Commun.* 91-94 (1999).

Alexander Steinbüchel et al., "Diversity of Bacterial Polyhydroxyalcanoic Acids," 128 *FEMS Microbiol. Lett.* 219-228 (1995).

C.D. Lytle et al., "Filtration Sizes of Human Immunodeficiency Virus Type 1 and Surrogate Viruses Used to Test Barrier Materials," 58 (2) *Appl. & Environm. Microbiol.* 747-749 (1992).

Richard Ashby et al., "A Tunable Switch to Regulate the Synthesis of Low and High Molecular Weight Microbal Polyesters," 62(1) *Biotechnol. Bioeng.* 106-113 (1999).

Leigh A. Madden et al., "Chain Termination in Polyhydroxyalkanoate Synthesis: Involvem nt of Exogenous Hydroxy-Compounds as Chain Transfer Agents," 25 *Intl. J. Biol. Macromol.* 43-53 (1999).

Gerhart Braunegg et al., "Polyhydroxyalkanoates, Biopolyesters from Renewable Resources: Physiological and Engineering Aspects," 65 *J. Biotechnol.* 127-161 (1998).

A. Steinbüchel et al., "Molecular Basis for Biosynthesis and Accumulation of Polyhydroxyalkanoic Acids in Bacteria," 103 *FEMS Microbiol. Rev.* 217-230 (1992).

Fengying Shi et al., "Use of Poly(ethylene glycol)s to Regulate Poly(3-hydroxybutyrate) Molecular Weight During *Alcaligenes eutrophus* Cultivations," 29 *Macromol.* 7753-7758 (1996).

Herbert Ulmer et al., "Bacterial Production of Poly(β-hydroxyalkanoates) Containing Unsaturated Repeating Units by *Rhodospirillum rubrum*," 27 *Macromol.* 1675-1679 (1994).

Marianela Andújar et al., "Polyesters Produced by *Pseudomonal oleovorans* Containing Cyclohexyl Groups," 30 *Macromol.* 1611-1615 (1997).

J.K. Stille et al., "Tetracyclic Dienes. I. The Diels-Alder Adduct of Norbornadiene and Cyclopentadiene," 81 *J. Am. Chem. Soc.* 4273-4275 (Aug. 1959).

G.J.M. de Koning et al., "A Biodegradable Rubber by Crosslinking Poly(Hydroxyalkanoate) From *Pseudomonas oleovorans*," 35(10) *Polymer* 2090-2097 (1994).

Moon Yeun Lee et al., "Crosslinking of Microbal Copolyesters with Pendant Epoxide Groups by Diamine," 40 *Polymer* 3787-3793 (1999).

M.Y. Lee et al., "Hydrophilic Bacterial Polyesters Modified with Pendant Hydroxyl Groups," 41 *Polymer* 1703-1709 (2000).

Safwat Antoun et al., "Production of Chiral Polyester by *Pseudomonas oleovorans* Grown with 5-Phenyl-2,4-Pentadienoic Acid," 3(6) *Chirality* 492-494 (1991).

Yoshiharu Doi et al., "Biosynthesis and Characterization of a New Bacterial Copolyester of 3-Hydroxyalkanoates and 3-Hydroxy-ω-Chloroalkanoates," 23 *Macromol.* 3705-3707 (1990).

Kuno Jung et al., "Characterization of New Bacterial Copolyesters Containing 3-Hydroxyalkanoates and Acetoxy-3-Hydroxyalkanoates," 33 *Macromol.* 8571-8575 (2000).

Alan Grund et al., "Regulation of Alkane Oxidation in *Pspeudomonas putida*," 123(2) *J. Bacteriol.* 546-556 (1975).

Katsutoshi Hori et al., "Production of Poly(3-Hydroxyalkanoates-co-3-Hydroxy-ω-Fluoroalkanoates) by *Pseudomonal oleovorans* from 1-Fluorononane and Gluconate," 16(5) *Biotechnol. Lett.* 501-506 (May 1994).

YoungBaek Kim et al., "Poly-3-hydroxyalkanoates Produced from *Pseudomonas oleovorans* Grown with ω-Polyhydroxyalkanoates," 29 *Macromol.* 3432-3435 (1996).

Yasuo Takagi et al., "Biosynthesis of Polyhydroxyalkanoate with a Thiophenoxy Side Groups Obtained from *Pseudomonas putida*," *Macromol.* 8315-8318 (1999).

Roland G. Lageveen et al., "Formation of Polyesters by *Pseudomonas oleoverans*: Effect of Substrates on Formation and Composition of Poly-(R)-3-Hydroxyalkanoates and Poly-(R)-3-Hydroxyalkenoates," 54(12) *Appl. Environ. Microbiol.* 2924-2932 (1988).

Marianela Andújar et al., "Polyesters Produced by *Pseudomonal oleovorans* Containing Cyclohexyl Groups," 30 *Macromol.* 1611-1615 (1997).

Won Ho Park et al., "Epoxidation of Bacterial Polyesters with Unsaturated Side Chains. I. Production and Epoxidation of Polyesters From 10-Undecanoic Acid," 31 *Macromol.* 1480-1486 (1998).

Won Ho Park et al., "Epoxidation of Bacterial Polyesters with Unsaturated Side Chains. II. Rate of Epoxidation and Polymer Properties," 36 *J. Polym. Sci.* 2381-2387 (1998).

* cited by examiner

POLYHYDROXYALKANOATE COPOLYMER INCLUDING UNIT HAVING BROMO GROUP IN SIDE CHAIN AND METHOD FOR PRODUCING THE SAME

BACKGROUND OF THE INVENTION

1. Field of the Invention

The present invention relates to a polyhydroxyalkanoate containing a novel unit and a producing method therefor utilizing microorganisms.

2. Related Background Art

"Biodegradable Plastics Handbook", edited by Biodegradable Plastics Association, N.T.S.Co., p 178–197 (1995) reports that various microorganisms produce poly-3-hydroxybutyric acid (PHB) or other polyhydroxyalkanoates (PHA) and accumulate such products therein. Such microorganism-produced polymers, for example PHA, can be utilized for producing various products, for example, by fusion, like the conventional plastics. Also, the microorganism-produced polymer, such as PHA, is biodegradable, and has an advantage in that it can be completely decomposed by the microorganisms. Therefore, polyhydroxyalkanoate produced by the microorganisms, when discarded, unlike the various conventional synthesized polymers, does not contaminate the environment. The polyhydroxyalkanoate produced by the microorganisms generally shows satisfactory compatibility with living tissues and is expected to be useful for medical applications as a soft material.

Such microorganism-produced PHA is known to assume various compositions or structures depending on the kind of microorganism, composition of the culture medium and culturing conditions employed for production. Various researches have been conducted to control such composition and structure, principally for improving the physical properties of PHA.

In one type of such researches, a microorganism production of a polyhydroxyalkanoate having an aromatic ring in the unit has been actively investigated in recent years.

(a) PHA containing phenyl group or a partially substituted group thereof:

Makromol. Chem. 191, 1957–1965 (1990) and Macromolecules, 24, 5256–5260 (1991) report that *Pseudomonas oleovorans* produces PHA containing 3-hydroxy-5-phenylvaleric acid as a unit, from 5-phenylvaleric acid as substrate.

Also Macromolecules, 29, 1762–1766 (1996) reports that *Pseudomonas oleovorans* produces PHA containing 3-hydroxy-5-(p-tolyl)valeric acid as a unit, from 5-(p-tolyl)valeric acid as substrate.

Also Macromolecules, 32, 2889–2895 (1999) reports that *Pseudomonas oleovorans* produces PHA containing 3-hydroxy-5-(2,4-dinitrophenyl)valeric acid and 3-hydroxy-5-(p-nitrophenyl)valeric acid as units, from 5-(2,4-dinitrophenyl)valeric acid as substrate.

(b) PHA containing phenoxy group or partially substituted group thereof:

Macromol. Chem. Phys., 195, 1665–1672 (1994) reports that *Pseudomonas oleovorans* produces a polyhydroxyalkanoate copolymer containing 3-hydroxy-5-hydroxyvaleric acid and 3-hydroxy-9-phenoxynonaic acid as the units, from 11-phenoxyundecanoic acid as substrate.

Also, Japanese Patent No. 2989175 discloses inventions relating to a homopolymer formed by a 3-hydroxy-5-(monofluorophenoxy)pentanoate (3H5(MFP)P) unit or a 3-hydroxy-5-(difluorophenoxy)pentanoate (3H5(DFP)P) unit; a copolymer containing at least a 3H5(MFP)P unit or a 3H5(DFP)P unit; a novel strain of *Pseudomonas putida* capable of producing these polymers; and a method for producing the aforementioned polymers utilizing the *Pseudomonas* genus. This patent specification teaches, as the effects of such inventions, that PHA polymer having a phenoxy group substituted with 1 or 2 fluorine atoms at the end of the side chain can be biosynthesized from a long-chain fatty acid having a substituent and that such a polymer has a high melting point and is capable of providing stereo-regularity and water repellency while maintaining satisfactory working properties.

In addition to the fluorine-substituted PHA having a fluorine substitution on an aromatic ring in a unit, there is also investigated a polyhydroxyalkanoate in which an aromatic in the unit is substituted with a cyano or nitro group.

Can. J. Microbiol., 41, 32–43 (1995) and Polymer International, 39, 205–213 (1996) report production of a polyhydroxyalkanoate containing 3-hydroxy-6-(p-cyanophenoxy) hexanoic acid or 3-hydroxy-6-(p-nitrophenoxy) hexanoic acid as the monomer unit by *Pseudomonas oleovorans* ATCC 29347 strain and *Pseudomonas putida* KT2442 stain, from octanoic acid and 6-(p-cyanophenoxy) hexanoic acid or 6-(p-nitrophenoxy) hexanoic acid as substrate.

A polyhydroxyalkanoate including a unit having an aromatic ring provided with a substituent constitutes a polyhydroxyalkanoate of multiple functions, including novel functions resulting from the substituent present on the aromatic ring, while retaining polymer properties of a high glass transition point and a satisfactory working property, resulting from the aromatic ring.

On the other hand, active investigations are conducted to obtain a polyhydroxyalkanoate of multiple functions, based on polyhydroxyalkanoate having a bromo group in the unit and introducing an arbitrary functional group into a side chain of the produced polymer, by a chemical conversion utilizing such a bromo group.

Macromol. Rapid Commun., 20, p. 91–94 (1999) reports producing polyhydroxyalkanoate having a bromo group in a side chain by *Pseudomonas oleovorans* and modifying the side chain with a thiolated product of acetylated maltose, thereby synthesizing a polyhydroxyalkanoate different in solubility or hydrophilicity.

As described in the foregoing references, a bromo group has a high reactivity in an addition reaction or the like, and can be used for introducing various functional groups or for chemical conversion. It can also constitute a cross-linking point, which is a starting point of a cross-linking reaction of the polymer. Consequently, the presence of a bromo group in a unit constituting a polyhydroxyalkanoate can be considered very useful in conceiving applications of the polymer as a functional material.

Such a polyhydroxyalkanoate having a bromo group in the unit has been biosynthesized from ω-bromoalkanoic acid only as the raw material, or in co-existence of a straight-chain alkanoic acid.

Macromolecules, 25, p. 1852–1857 (1992), reports that the *Pseudomonas oleovorans* strain produces a polyhydroxyalkanoate containing a 3-hydroxy-ω-alkanoic acid, unit in the co-existence of an ω-bromoalkanoic acid such as 11-bromoundecanoic acid, 8-bromooctanoic acid or 6-bromohexanoic acid and n-nonanoic acid.

In addition to the foregoing, Japanese Patent Application Laid-Open No. 2001-288256 is cited in the present application.

However, thus obtained polyhydroxyalkanoate having a bromo group in the unit is usually a copolymer including a straight-chain 3-hydroxyalkanoic acid unit. Such PHA has a glass transition temperature of −20° C. to −30° C., so that the application as a polymer is limited. Because of this limitation, a polyhydroxyalkanoate having a bromo group in the unit, which is thermally so stable as to expand the field of application as a polymer and which also allows to arbitrarily control physical properties, and a producing method therefor are desired.

SUMMARY OF THE INVENTION

The present inventors, as a result of intensive investigations to achieve the above-mentioned objectives, have made the following invention. More specifically, the present invention provides:

(A) a polyhydroxyalkanoate copolymer including a 3-hydroxy-ω-bromoalkanoic acid unit represented by a chemical formula (1) and a unit represented by a chemical formula (2) within a same molecule:

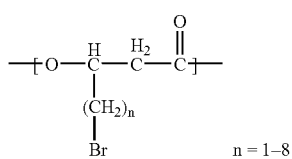

(1)

wherein n designates a number within a range shown in the chemical formula and can be different from that of another unit in the same molecule;

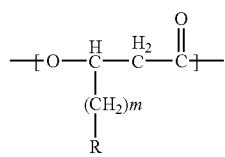

(2)

wherein a pair of R and m is selected from the group consisting of R including a residue having a phenyl structure and m being an integer selected from 1 to 8, R including a residue having a thienyl structure and m being an integer selected from 1 to 8; and R including a residue having a cyclohexyl structure and m being an integer selected from 0 to 8; and, in case plural units are present, the pair of R and m of one unit can be different from that of another unit in the same molecule.

The polyhydroxyalkanoate copolymer of the present invention is:

(B) a polyhydroxyalkanoate copolymer according to (A) wherein R in the unit represented by the foregoing chemical formula (2), namely a residue having a phenyl, thienyl or cyclohexyl structure is at least one selected from the group consisting of the following chemical formulas (3) to (14) and, in case plural units are present, can be different from that of another unit in the same molecule:

(3)

wherein $R_1$ designates a substituent on the aromatic ring selected from the group consisting of an H atom, a halogen atom, CN, $NO_2$, $CH_3$, $C_2H_5$, $C_3H_7$, $CH=CH_2$, $COOR_2$ (wherein $R_2$ is selected from the group consisting of an H atom, a Na atom and a K atom), $CF_3$, $C_2F_5$ and $C_3F_7$, and, in case plural units are present, can be different from that of another unit in the same molecule;

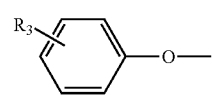

(4)

wherein $R_3$ designates a substituent on the aromatic ring selected from the group consisting of an H atom, a halogen atom, CN, $NO_2$, $CH_3$, $C_2H_5$, $C_3H_7$, $CF_3$, $C_2F_5$, $C_3F_7$, and $SCH_3$, and, in case plural units are present, can be different from that of another unit in the same molecule;

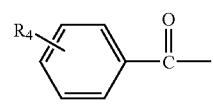

(5)

wherein $R_4$ designates a substituent on the aromatic ring selected from the group consisting of an H atom, a halogen atom, CN, $NO_2$, $CH_3$, $C_2H_5$, $C_3H_7$, $CF_3$, $C_2F_5$ and $C_3F_7$, and, in case plural units are present, can be different from that of another unit in the same molecule;

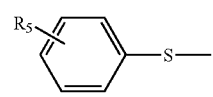

(6)

wherein $R_5$ designates a substituent on the aromatic ring selected from the group consisting of an H atom, a halogen atom, CN, $NO_2$, $COOR_6$, $SO_2R_7$ (wherein $R_6$ is selected from the group consisting of an H atom, a Na atom, a K atom, $CH_3$ and $C_2H_5$, and $R_7$ is selected from the group consisting of OH, ONa, OK, a halogen atom, $OCH_3$ and $OC_2H_5$), $CH_3$, $C_2H_5$, $C_3H_7$, $(CH_3)_2$—CH and $(CH_3)_3$—C, and, in case plural units are present, can be different from that of another unit in the same molecule;

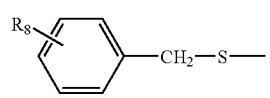

(7)

wherein $R_8$ designates a substituent on the aromatic ring selected from the group consisting of an H atom, a halogen atom, CN, NO$_2$, COOR$_9$, SO$_2$R$_{10}$ (wherein R$_9$ is selected from the group consisting of an H atom, a Na atom, a K atom, CH$_3$ and C$_2$H$_5$, and R$_{10}$ is selected from the group consisting of OH, ONa, OK, a halogen atom, OCH$_3$ and OC$_2$H$_5$), CH$_3$, C$_2$H$_5$, C$_3$H$_7$, (CH$_3$)$_2$—CH and (CH$_3$)$_3$—C, and, in case plural units are present, can be different from that of another unit in the same molecule;

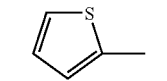
(8)

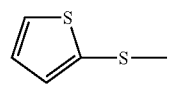
(9)

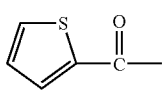
(10)

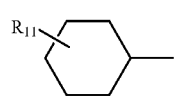
(11)

wherein R$_{11}$ designates a substituent on the cyclohexyl group selected from the group consisting of an H atom, CN, NO$_2$, a halogen atom, CH$_3$, C$_2$H$_5$, C$_3$H$_7$, CF$_3$, C$_2$F$_5$, and C$_3$F$_7$, and, in case plural units are present, can be different from that of another unit in the same molecule;

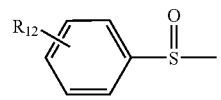
(12)

wherein R$_{12}$ designates a substituent on the aromatic ring selected from the group consisting of an H atom, a halogen atom, CN, NO$_2$, COOR$_{13}$, SO$_2$R$_{14}$ (wherein R$_{13}$ is selected from the group consisting of an H atom, a Na atom, a K atom, CH$_3$ and C$_2$H$_5$, and R$_{14}$ is selected from the group consisting of OH, ONa, OK, a halogen atom, OCH$_3$ and OC$_2$H$_5$), CH$_3$, C$_2$H$_5$, C$_3$H$_7$, (CH$_3$)$_2$—CH and (CH$_3$)$_3$—C, and, in case plural units are present, can be different from that of another unit in the same molecule;

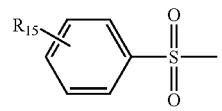
(13)

wherein R$_{15}$ designates a substituent on the aromatic ring selected from the group consisting of an H atom, a halogen atom, CN, NO$_2$, COOR$_{16}$, SO$_2$R$_{17}$ (wherein R$_{16}$ is selected from the group consisting of an H atom, a Na atom, a K atom, CH$_3$ and C$_2$H$_5$, and R$_{17}$ is selected from the group consisting of OH, ONa, OK, a halogen atom, OCH$_3$ and OC$_2$H$_5$), CH$_3$, C$_2$H$_5$, C$_3$H$_7$, (CH$_3$)$_2$—CH and (CH$_3$)$_3$—C, and, in case plural units are present, can be different from that of another unit in the same molecule;

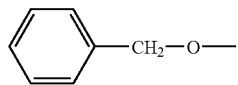
(14)

The polyhydroxyalkanoate copolymer of the present invention is:

(C) a polyhydroxyalkanoate copolymer according to (A) or (B), wherein the 3-hydroxy-ω-bromoalkanoic acid unit represented by the foregoing chemical formula (1) is at least either of a 3-hydroxy-8-bromooctanoic acid unit represented by a chemical formula (15) and a 3-hydroxy-6-bromohexanoic acid unit represented by a chemical formula (16), and, in case plural units are present, can be different from that of another unit in the same molecule:

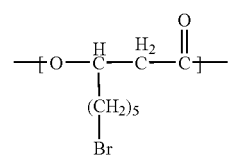
(15)

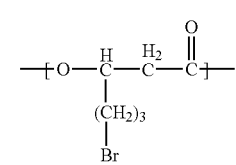
(16)

Also the polyhydroxyalkanoate copolymer of the present invention is:

(D) a polyhydroxyalkanoate copolymer according to (A) or (B), wherein the 3-hydroxy-ω-bromoalkanoic acid unit represented by the foregoing chemical formula (1) is at least one of a 3-hydroxy-11-bromoundecanoic acid unit represented by a chemical formula (17), a 3-hydroxy-9-bromoundecanoic acid unit represented by a chemical formula (18) and a 3-hydroxy-7-bromoheptanoic acid unit represented by a chemical formula (19), and, in case plural units are present, can be different from that of another unit in the same molecule:

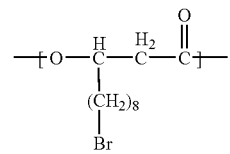
(17)

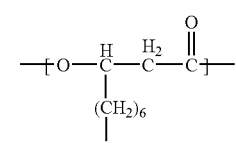
(18)

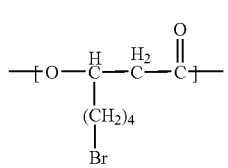
(19)

The polyhydroxyalkanoate copolymer of the present invention is:

(E) a polyhydroxyalkanoate copolymer having a number-average molecular weight within a range from 2,000 to 500,000.

The present invention also provides:

(F) a method for producing a polyhydroxyalkanoate copolymer including at least a kind of a 3-hydroxy-ω-bromoalkanoic acid unit represented by the chemical formula (1) and at least a kind of a unit represented by the chemical formula (2) within a same molecule, comprising the step of executing a biosynthesis by a microorganism having an ability of producing a polyhydroxyalkanoate copolymer including a 3-hydroxy-ω-bromoalkanoic acid unit represented by the chemical formula (1) and a unit represented by the chemical formula (2) within a same molecule, wherein at least a kind of ω-bromoalkanoic acid represented by a chemical formula (20) and at least a kind of a compound represented by a chemical formula (21) is utilized as the raw materials:

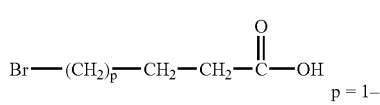
(20)

wherein p is an integer selected within a range indicated in the chemical formula,

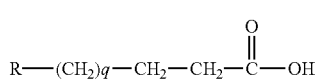
(21)

wherein a pair of R and q is selected from the group consisting of R including a residue having a phenyl structure and q being an integer selected from 1 to 8, R including a residue having a thienyl structure and q being an integer selected from 1 to 8, and R including a residue having a cyclohexyl structure and q being an integer selected from 0 to 8,

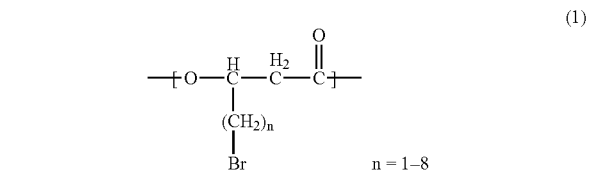
(1)

wherein n designates, independently for each unit, a number within a range shown in the chemical formula,

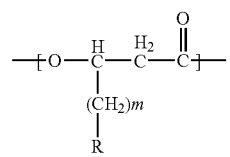
(2)

wherein a pair of R and m is selected from the group consisting of R including a residue having a phenyl structure and m being an integer selected from 1 to 8, R including a residue having a thienyl structure and m being an integer selected from 1 to 8, and R including a residue having a cyclohexyl structure and m being an integer selected from 0 to 8, and, in case plural units are present, the pair of R and m of one unit can be different from that of another unit in the same molecule.

The method for producing polyhydroxyalkanoate copolymer of the present invention is:

(G) a method for producing a polyhydroxyalkanoate copolymer according to (F) wherein R in the unit represented by the foregoing chemical formulas (2) and (21), namely a residue having a phenyl, thienyl or cyclohexyl structure is at least one selected from the group consisting of the following chemical formulas (3) to (14) and, in case plural units are present, can be different from that of another unit in the same molecule:

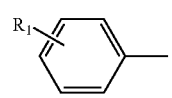
(3)

wherein $R_1$ designates a substituent on the aromatic ring selected from the group consisting of an H atom, a halogen atom, CN, $NO_2$, $CH_3$, $C_2H_5$, $C_3H_7$, $CH=CH_2$, $COOR_2$ (wherein $R_2$ is selected from the group consisting of an H atom, a Na atom and a K atom), $CF_3$, $C_2F_5$ and $C_3F_7$, and, in case plural units are present, can be different from that of another unit in the same molecule;

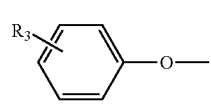
(4)

wherein $R_3$ designates a substituent on the aromatic ring selected from the group consisting of an H atom, a halogen atom, CN, $NO_2$, $CH_3$, $C_2H_5$, $C_3H_7$, $CF_3$, $C_2F_5$, $C_3F_7$, and $SCH_3$, and, in case plural units are present, can be different from that of another unit in the same molecule;

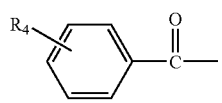
(5)

wherein $R_4$ designates a substituent on the aromatic ring selected from the group consisting of an H atom, a halogen atom, CN, NO$_2$, CH$_3$, C$_2$H$_5$, C$_3$H$_7$, CF$_3$, C$_2$F$_5$ and C$_3$F$_7$, and, in case plural units are present, can be different from that of another unit in the same molecule;

(6)

wherein R$_5$ designates a substituent on the aromatic ring selected from the group consisting of an H atom, a halogen atom, CN, NO$_2$, COOR$_6$, SO$_2$R$_7$ (wherein R$_6$ is selected from the group consisting of an H atom, a Na atom, a K atom, CH$_3$ and C$_2$H$_5$, and R$_7$ is selected from the group consisting of OH, ONa, OK, a halogen atom, OCH$_3$ and OC$_2$H$_5$), CH$_3$, C$_2$H$_5$, C$_3$H$_7$, (CH$_3$)$_2$—CH and (CH$_3$)$_3$—C, and, in case plural units are present, can be different from that of another unit in the same molecule;

(7)

wherein R$_8$ designates a substituent on the aromatic ring selected from the group consisting of an H atom, a halogen atom, CN, NO$_2$, COOR$_9$, SO$_2$R$_{10}$ (wherein R$_9$ is selected from the group consisting of an H atom, a Na atom, a K atom, CH$_3$ and C$_2$H$_5$, and R$_{10}$ is selected from the group consisting of OH, ONa, OK, a halogen atom, OCH$_3$ and OC$_2$H$_5$), CH$_3$, C$_2$H$_5$, C$_3$H$_7$, (CH$_3$)$_2$—CH and (CH$_3$)$_3$—C, and, in case plural units are present, can be different from that of another unit in the same molecule;

(8)

(9)

(10)

(11)

wherein R$_{11}$ designates a substituent on the cyclohexyl group and is selected from the group consisting of an H atom, CN, NO$_2$, a halogen atom, CH$_3$, C$_2$H$_5$, C$_3$H$_7$, CF$_3$, C$_2$F$_5$, and C$_3$F$_7$, and, in case plural units are present, can be different from that of another unit in the same molecule;

(12)

wherein R$_{12}$ designates a substituent on the aromatic ring selected from the group consisting of an H atom, a halogen atom, CN, NO$_2$, COOR$_{13}$, SO$_2$R$_{14}$ (wherein R$_{13}$ is selected from the group consisting of an H atom, a Na atom, a K atom, CH$_3$ and C$_2$H$_5$, and R$_{14}$ is selected from the group consisting of OH, ONa, OK, a halogen atom, OCH$_3$ and OC$_2$H$_5$), CH$_3$, C$_2$H$_5$, C$_3$H$_7$, (CH$_3$)$_2$—CH and (CH$_3$)$_3$—C, and, in case plural units are present, can be different from that of another unit in the same molecule;

(13)

wherein R$_{15}$ designates a substituent on the aromatic ring selected from the group consisting of an H atom, a halogen atom, CN, NO$_2$, COOR$_{16}$, SO$_2$R$_{17}$ (wherein R$_{16}$ is selected from the group consisting of an H atom, a Na atom, a K atom, CH$_3$ and C$_2$H$_5$, and R$_{17}$ is selected from the group consisting of OH, ONa, OK, a halogen atom, OCH$_3$ and OC$_2$H$_5$), CH$_3$, C$_2$H$_5$, C$_3$H$_7$, (CH$_3$)$_2$—CH and (CH$_3$)$_3$—C, and, in case plural units are present, can be different from that of another unit in the same molecule;

(14)

The method for producing polyhydroxyalkanoate copolymer of the present invention can be:

(H) a method for producing a polyhydroxyalkanoate copolymer according to (F) or (G) by culturing the aforementioned microorganisms in a culture medium including at least a kind of ω-bromoalkanoic acid represented by the foregoing chemical formula (20) and at least a kind of a compound represented by the foregoing chemical formula (21).

More specifically, the method for producing polyhydroxyalkanoate copolymer of the present invention can be a method for producing a polyhydroxyalkanoate copolymer featured by culturing the aforementioned microorganisms in a culture medium including a peptide in addition to at least a kind of ω-bromoalkanoic acid represented by the foregoing chemical formula (20) and at least a kind of a compound represented by the foregoing chemical formula (21). In such a case, there is provided a method for producing a polyhydroxyalkanoate copolymer featured by employing polypeptone as the aforementioned peptide to be included in the culture medium.

Also, the method for producing a polyhydroxyalkanoate copolymer of the present invention can be a method for producing a polyhydroxyalkanoate copolymer featured by culturing the aforementioned microorganisms in a culture medium including a yeast extract in addition to at least a kind of ω-bromoalkanoic acid represented by the foregoing chemical formula (20) and at least a kind of a compound represented by the foregoing chemical formula (21).

Also, the method for producing a polyhydroxyalkanoate copolymer of the present invention can be a method for producing a polyhydroxyalkanoate copolymer featured by culturing the aforementioned microorganisms in a culture medium including an organic acid or a salt thereof in addition to at least a kind of ω-bromoalkanoic acid represented by the foregoing chemical formula (20) and at least a kind of a compound represented by the foregoing chemical formula (21). In such a case, there can be provided a method for producing a polyhydroxyalkanoate copolymer featured by utilizing, as the organic acid or the salt thereof to be included in the culture medium, at least one selected from the group consisting of pyruvic acid, oxaloacetic acid, citric acid, isocitric acid, ketoglutaric acid, succinic acid, fumaric acid, malic acid, lactic acid and salts thereof.

Also, the method for producing a polyhydroxyalkanoate copolymer of the present invention can be a method for producing a polyhydroxyalkanoate copolymer featured by culturing the aforementioned microorganisms in a culture medium including an amino acid or a salt thereof in addition to at least a kind of ω-bromoalkanoic acid represented by the foregoing chemical formula (20) and at least a kind of a compound represented by the foregoing chemical formula (21). In such a case, there can be realized a method for producing a polyhydroxyalkanoate copolymer featured by utilizing, as the amino acid or the salt thereof to be included in the culture medium, at least one selected from the group consisting of glutamic acid, aspartic acid and salts thereof.

Also, the method for producing a polyhydroxyalkanoate copolymer of the present invention can be a method for producing a polyhydroxyalkanoate copolymer featured by culturing the aforementioned microorganisms in a culture medium including a sugar, in addition to at least a kind of ω-bromoalkanoic acid represented by the foregoing chemical formula (20) and at least a kind of a compound represented by the foregoing chemical formula (21). In such a case, there can be realized a method for producing a polyhydroxyalkanoate copolymer featured by utilizing, as the sugar to be included in the culture medium, at least one compound selected from the group consisting of glyceroaldehyde, erythrose, arabinose, xylose, glucose, galactose, mannose, fructose, glycerol, erythritol, xylitol, gluconic acid, glucuronic acid, galactronic acid, maltose, sucrose and lactose.

Also, the method for producing a polyhydroxyalkanoate copolymer of the present invention can be a method for producing a polyhydroxyalkanoate copolymer featured by culturing the aforementioned microorganisms in a culture medium including a straight-chain alkanoic acid with 4 to 12 carbon atoms or a salt thereof in addition to at least a kind of ω-bromoalkanoic acid represented by the foregoing chemical formula (20) and at least a kind of a compound represented by the foregoing chemical formula (21).

The details of culturing conditions for the microorganisms in the producing method of the polyhydroxyalkanoate of the present invention will be discussed below.

In an inorganic culture medium based on a phosphate buffer and an ammonium salt or a nitrate salt, various necessary substrates and nutrition sources are added.

As the substrate for producing the desired polyhydroxyalkanoate copolymer, there are preferably contained at least a kind of ω-bromoalkanoic acid represented by the foregoing chemical formula (20) and at least a kind of a compound represented by the foregoing chemical formula (21), each in amount of 0.0005 to 1% (w/v) of the medium, more preferably 0.001 to 0.2%.

A carbon source and a nitrogen source for microorganism proliferation, namely co-existing substrates as energy sources for producing the polyhydroxyalkanoate copolymer, are preferably contained in a concentration within a range of 0.1 to 5% (w/v) per medium, more preferably 0.2 to 2% (w/v).

The culture medium to be employed in the present invention can be any inorganic culture medium, a phosphate salt and a nitrogen source, such as an ammonium salt or a nitrate salt, but the productivity of the polyhydroxyalkanoate copolymer can be improved by regulating the concentration of the nitrogen source.

The culture temperature can be any temperature at which the aforementioned strains can satisfactorily proliferate, and is preferably within a range of 15 to 37° C., more preferably 20 to 30° C.

The culture can be obtained using any culture method, such as a liquid culture or a solid culture, in which the employed microorganisms can proliferate and can produce a polyhydroxyalkanoate copolymer. Also there can be employed any one of a batch culture, a fed batch culture, a semi-continuous culture or a continuous culture. Also, for the liquid batch culture, there can be employed an oxygen supply method by shaking in a shaking flask or by agitated aeration in a jar fermenter.

For causing the microorganisms to produce and accumulate the polyhydroxyalkanoate copolymer, there can be employed, in addition to the above-described method, a method of transferring the bacteria after sufficient proliferation to a culture medium in which the nitrogen source, such as ammonium chloride, is limited, and executing a further culture under an addition of a compound serving as a substrate for the desired unit, whereby the productivity can be improved.

Also the producing method of the present invention can be a method for producing a polyhydroxyalkanoate copolymer, including steps of culturing the aforementioned microorganisms under the aforementioned conditions, and recovering from the cells thereof the polyhydroxyalkanoate copolymer including the 3-hydroxy-ω-bromoalkanoic acid unit represented by the chemical formula (1) and the unit represented by the chemical formula (2) within a same molecule.

DETAILED DESCRIPTION OF THE PREFERRED EMBODIMENTS

Method of Recovery

Figure 1:
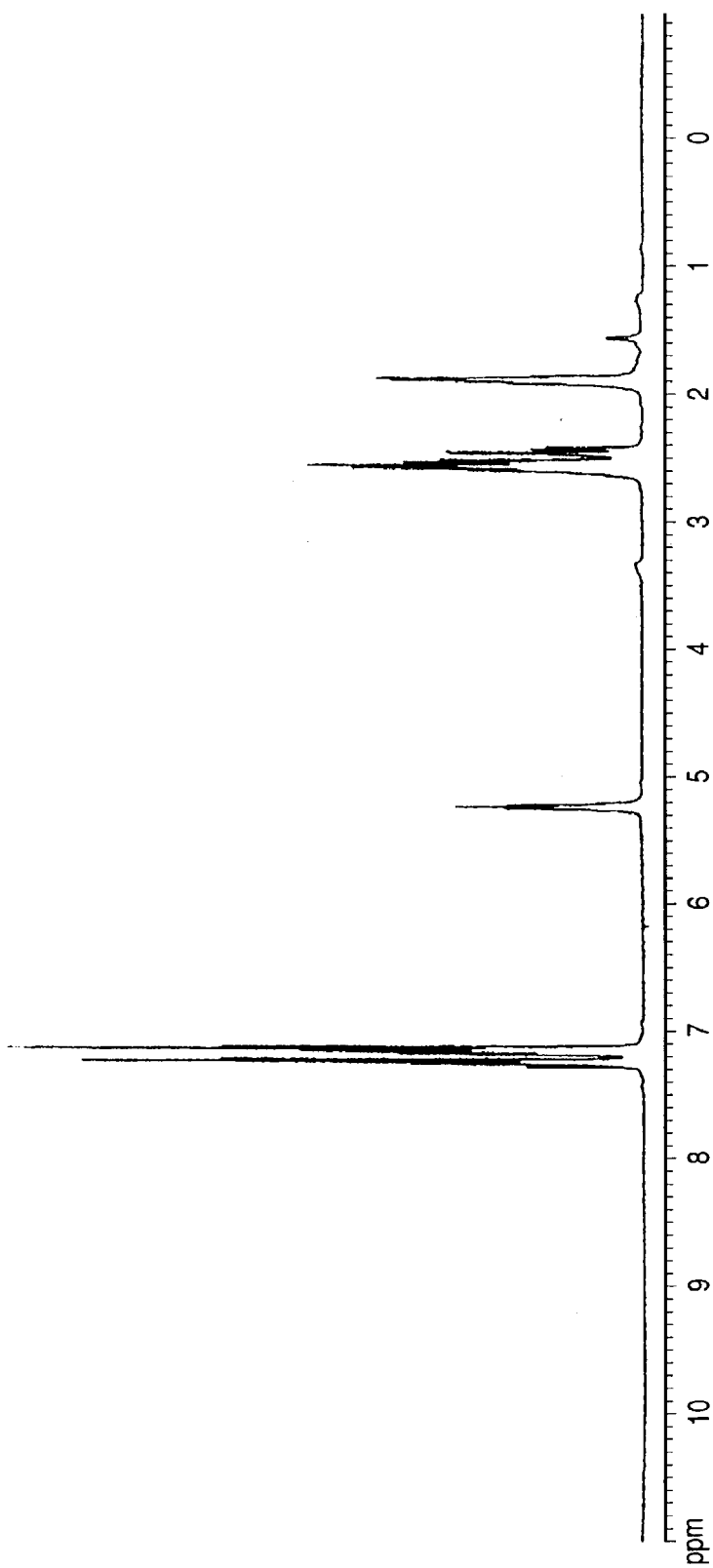
FIG. 1 is a chart showing the $^1$H-NMR spectrum of a polyester obtained in Example 1.

For recovering a desired polyhydroxyalkanoate copolymer from microbial cells, there can be applied an ordinary method for recovering a polyhydroxyalkanoate. Recovery is most simply executed by extraction with an organic solvent, such as chloroform, dichloromethane or acetone, but there may also be employed dioxane, tetrahydrdofuran or acetonitrile. In a situation where the organic solvent is difficult to use, there can be utilized processing with a surfactant, such as SDS, processing with an enzyme such as a lysozyme, chemical processing with a hypochlorite salt, ammonia or EDTA, or physical crushing by an ultrasonic crushing method, a homogenizer method, a pressure crushing method, a beads impact method, a mechanical crushing method, a grinding method or a freeze-thawing method to eliminate the bacteria components other than the polyhydroxyalkanoate copolymer, thereby recovering the polyhydroxyalkanoate copolymer.

Microorganisms

The microorganism to be employed in the producing method of the present invention can be any microorganism that meets the aforementioned requirements. However, microorganisms of the genus Pseudomonas are particularly preferred Specifically, such microorganisms are Pseudomonas cichorii, Pseudomonas putida, Pseudomonas fluorescens, Pseudomonas oleovorans, Pseudomonas aeruginosa, Pseudomonas stutzeri, Pseudomonas jessenii etc. More specifically, there can be used the following strains Pseudomonas cichorii YN2 (FERM BP-7375), Pseudomonas cichorii H45 (FERM BP-7374), Pseudomonas jessenii P161 (FERM BP-7376), and Pseudomonas putida P91 (FERM BP-7373). These four strains are deposited in International Patent Organism Depositary of National Institute of Advanced Industrial Science and Technology (former National Institute of Bioscience and Human-Technology, Agency of Industrial Science and Technology), and described in Japanese Patent Application Laid-Open No. 2001-288256 (patent reference 2).

The culturing of the microorganisms of the present invention, the production and microbial accumulation of the polyhydroxyalkanoate copolymer of the present invention, and the recovery of the polyhydroxyalkanoate from the microbial cells in the present invention are not limited to the methods described above.

Culture Medium

A composition of an inorganic culture medium (M9 medium), which is used in a method of the present invention, is shown in the following:

$Na_2HPO_4$: 6.3

$KH_2PO_4$: 3.0

$NH_4Cl$: 1.0

NaCl: 0.5

(g/L; pH 7.0)

It is necessary to add a stock solution of trace ingredients of the following composition to about 0.3% (v/v) to the above inorganic culture medium for good proliferation and production of the polyhydroxyalkanoate copolymer.

Stock solution of trace ingredients Nitrilotriacetic acid: 1.5; $MgSO_4$: 3.0; $MnSO_4$: 0.5; NaCl: 1.0; $FeSO_4$: 0.1; $CaCl_2$: 0.1; $CoCl_2$: 0.1; $ZnSO_4$: 0.1; $CuSO_4$: 0.1; $AlK(SO_4)_2$: 0.1; $H_3BO_3$: 0.1; $Na_2MoO_4$: 0.1; $NiCl_2$: 0.1 (g/L).

EXAMPLES

The present invention will now be described with reference to the following examples. In the following, "%" is based on weight, unless otherwise specified.

Example 1

5.0 g of polypeptone (supplied by Wako Pure Chemical Co.), 1.06 g of 5-phenylvaleric acid and 0.67 g of 8-bromooctanoic acid were dissolved in 1000 ml of the M9 culture medium, which was then charged in a 2000 ml shaking flask, sterilized in an autoclave and cooled to room temperature. To thus prepared culture medium, 5 ml of a culture liquid of Pseudomonas jessenii P161 strain, which was cultured with shaking in advance for 8 hours at 30° C. in an M9 culture medium containing 0.5% of polypeptone, was added and the culture was performed for 64 hours at 30° C. After culturing, bacteria cells were harvested by centrifuging, then washed with methanol and lyophilized. After a weight measurement of the bacteria cells, chloroform was added and stirring was conducted for 72 hours at 25° C. to extract the polymer. The chloroform containing the extracted polymer was filtered, then concentrated with an evaporator, and a portion precipitated and solidified by cold methanol was collected and dried under a reduced pressure to obtain the desired polymer.

A structure determination of the obtained polymer by $^1$H-NMR (FT-NMR:Bruker DPX400, 1H resonance frequency:400 MHz, measured nucleus species:1H, solvent: $CDCl_3$, reference:capillary-sealed $TMS/CDCl_3$, measurement temperature:room temperature) confirmed a polyhydroxyalkanoate copolymer (A:B:C+D=2:92:6) containing a unit represented by the following chemical formula (22). Also, $^{13}$C-NMR confirmed the presence of unit C (3-hydroxy-6-bromohexanoic acid unit) and unit D (3-hydroxy-8-bromooctaonic acid, but the ratio of the unit C and the unit D was unknown.

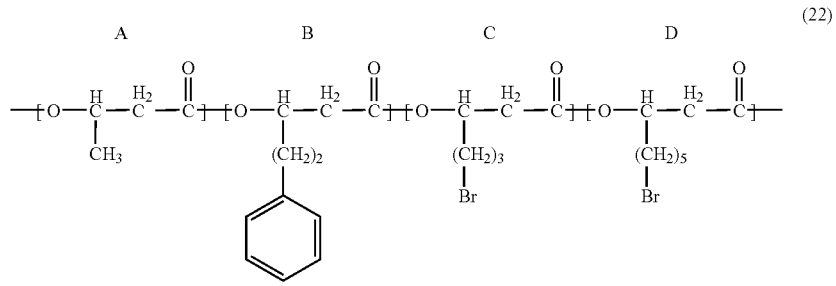

(22)

The molecular weight of the polymer was measured by gel permeation chromatography (GPC) (Tosoh HLC-8220, column: Tosoh TSK-GEL Super HM-H, solvent: chloroform, conversion to polystyrene).

FIG. 1 shows the $^1$H-NMR spectrum of the obtained polymer. Table 1 shows weights of cells and the polymer, a polymer weight ratio to cells, a molecular weight and a molecular weight distribution of the obtained polymer.

TABLE 1

| CDW (mg/L) | PDW (mg/L) | P/C % | Mn × $10^4$ | Mw × $10^4$ | Mw/Mn |
|---|---|---|---|---|---|
| 398 | 104 | 26.1 | 3.4 | 6.5 | 1.9 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 2

A process was executed in the same manner as in Example 1, except that the P161 strain used therein was changed to *Pseudomonas cichorii* YN2, to obtain a desired polymer.

A structure determination of the obtained polymer by $^1$H-NMR and $^{13}$C-NMR as in Example 1 confirmed a polyhydroxyalkanoate copolymer (A:B:C+D=1:90:9) containing a unit represented by the following chemical formula (23). Also, $^{13}$C-NMR confirmed the presence of unit C (3-hydroxy-6-bromohexanoic acid unit) and unit D (3-hydroxy-8-bromooctaonic acid unit), but the ratio of the unit C and the unit D was unknown.

The molecular weight of the polymer was measured by GPC as in Example 1.

Figure 2:
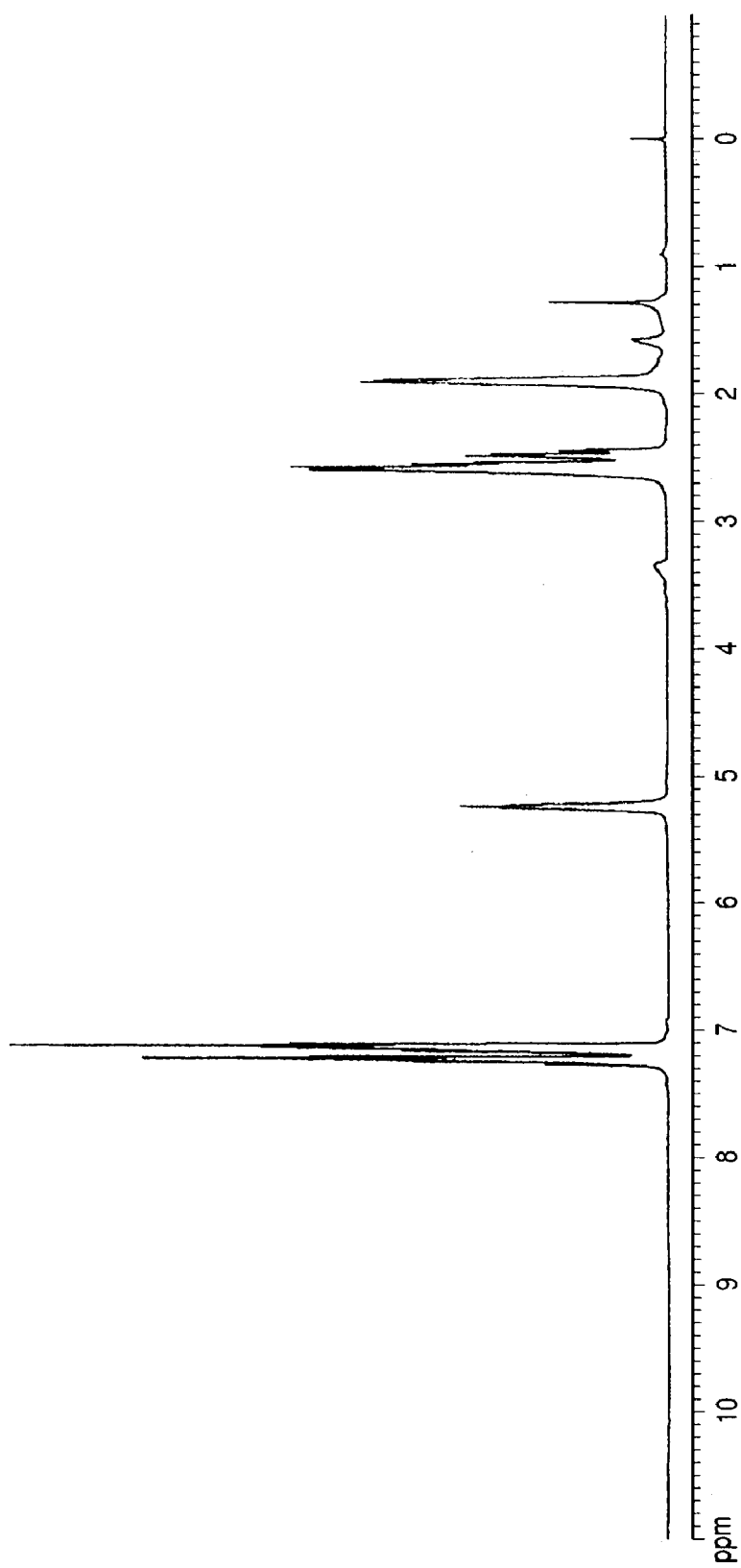
FIG. 2 is a chart showing the $^1$H-NMR spectrum of a polyester obtained in Example 2.

FIG. 2 shows the $^1$H-NMR spectrum of the obtained polymer. Table 2 shows weights of cells and the polymer, a polymer weight ratio to cells, a molecular weight and a molecular weight distribution of the obtained polymer.

TABLE 2

| CDW (mg/L) | PDW (mg/L) | P/C % | Mn × $10^4$ | Mw × $10^4$ | Mw/Mn |
|---|---|---|---|---|---|
| 821 | 271 | 33.0 | 6.6 | 13.9 | 2.1 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 3

A process was executed in the same manner as in Example 1, except that a polypeptone used therein was changed to yeast extract, to obtain a desired polymer. A structure determination of the obtained polymer by $^1$H-NMR and $^{13}$C-NMR as in Example 1 confirmed a polyhydroxyalkanoate copolymer (A:B:C+D=1:91:8) containing a unit represented by the following chemical formula (24). Also, $^{13}$C-NMR confirmed the presence of unit C (3-hydroxy-6-bromohexanoic acid unit) and unit D (3-hydroxy-8-bromooctaonic acid unit), but the ratio of the unit C and the unit D was unknown.

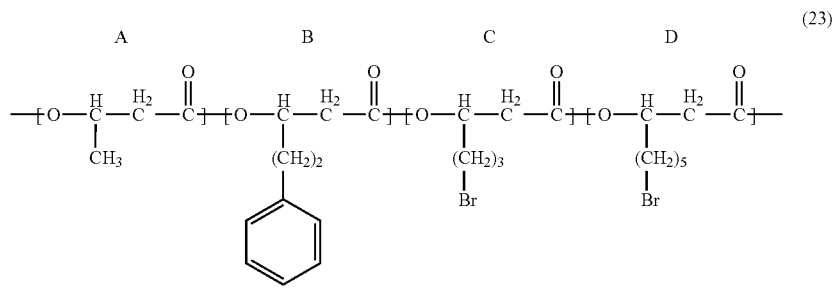

(23)

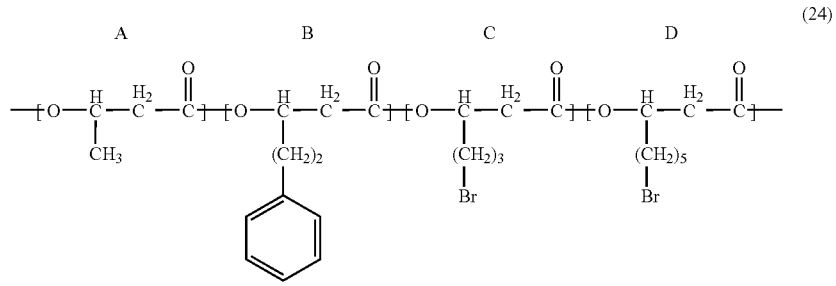

(24)

The molecular weight of the polymer was measured by GPC as in Example 1.

Table 3 shows weights of cells and the polymer, a polymer weight ratio to cells, a molecular weight and a molecular weight distribution of the obtained polymer.

TABLE 3

| CDW (mg/L) | PDW (mg/L) | P/C % | Mn × $10^4$ | Mw × $10^4$ | Mw/Mn |
|---|---|---|---|---|---|
| 388 | 99 | 25.5 | 3.3 | 6.6 | 2.0 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 4

A process was executed in the same manner as in Example 1, except that the P161 strain used therein was changed to *Pseudomonas cichorii* H45, to obtain a desired polymer. A structure determination of the obtained polymer by $^1$H-NMR and $^{13}$C-NMR as in Example 1 confirmed a polyhydroxyalkanoate copolymer (A:B:C+D=1:93:6) containing a unit represented by the following chemical formula (25). Also, $^{13}$C-NMR confirmed the presence of unit C (3-hydroxy-6-bromohexanoic acid unit) and unit D (3-hydroxy-8-bromooctaonic acid unit), but the ratio of the unit C and the unit D was unknown.

The molecular weight of the polymer was measured by GPC as in Example 1.

Table 4 shows weights of cells and the polymer, a polymer weight ratio to cells, a molecular weight and a molecular weight distribution of the obtained polymer.

TABLE 4

| CDW (mg/L) | PDW (mg/L) | P/C % | Mn × $10^4$ | Mw × $10^4$ | Mw/Mn |
|---|---|---|---|---|---|
| 312 | 81 | 26.0 | 3.6 | 6.9 | 1.9 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 5

A process was executed in the same manner as in Example 1, except that the P161 strain used therein was changed to *Pseudomonas putida* P91 and polypeptone in the culture medium was changed to yeast extract, to obtain a desired polymer. A structure determination of the obtained polymer by $^1$H-NMR and $^{13}$C-NMR as in Example 1 confirmed a polyhydroxyalkanoate copolymer (A:B:C+D=1:91:8) containing a unit represented by the following chemical formula (26). Also, $^{13}$C-NMR confirmed the presence of unit C (3-hydroxy-6-bromohexanoic acid unit) and unit D (3-hydroxy-8-bromooctaonic acid unit), but the ratio of the unit C and the unit D was unknown.

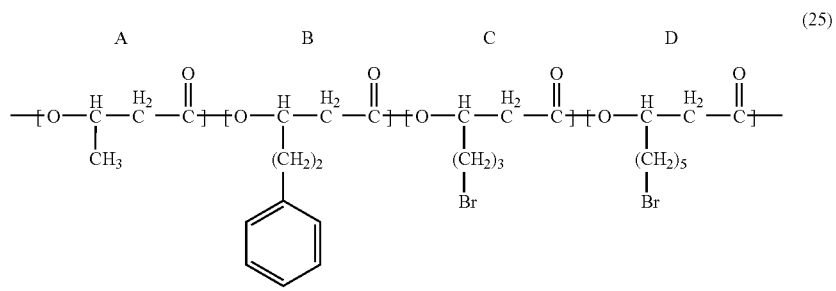

(25)

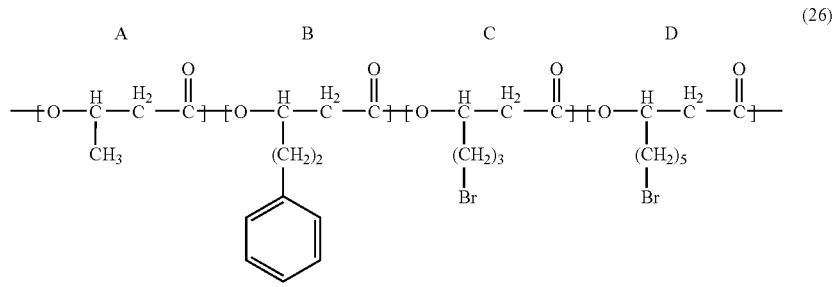

(26)

The molecular weight of the polymer was measured by GPC as in Example 1.

Table 5 shows weights of cells and the polymer, a polymer weight ratio to cells, a molecular weight and a molecular weight distribution of the obtained polymer.

TABLE 5

| CDW (mg/L) | PDW (mg/L) | P/C % | Mn × $10^4$ | Mw × $10^4$ | Mw/Mn |
|---|---|---|---|---|---|
| 2.12 | 59 | 27.8 | 4.0 | 7.8 | 2.0 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 6

A process was executed in the same manner as in Example 1, except that the polypeptone in the culture medium was changed to D-glucose, to obtain a desired polymer. A structure determination of the obtained polymer by $^1$H-NMR and $^{13}$C-NMR as in Example 1 confirmed a polyhydroxyalkanoate copolymer (A:B:C+D=3:90:7) containing a unit represented by the following chemical formula (27). Also, $^{13}$C-NMR confirmed the presence of unit C (3-hydroxy-6-bromohexanoic acid unit) and unit D (3-hydroxy-8-bromooctaonic acid unit), but the ratio of the unit C and the unit D was unknown.

The molecular weight of the polymer was measured by GPC as in Example 1.

Table 6 shows weights of cells and the polymer, a polymer weight ratio to cells, a molecular weight and a molecular weight distribution of the obtained polymer.

TABLE 6

| CDW (mg/L) | PDW (mg/L) | P/C % | Mn × $10^4$ | Mw × $10^4$ | Mw/Mn |
|---|---|---|---|---|---|
| 507 | 161 | 31.6 | 3.7 | 7.8 | 2.1 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 7

A process was executed in the same manner as in Example 1, except that the polypeptone in the culture medium was changed to sodium pyruvate, to obtain a desired polymer. A structure determination of the obtained polymer by $^1$H-NMR and $^{13}$C-NMR as in Example 1 confirmed a polyhydroxyalkanoate copolymer (A:B:C+D=4:89:7) containing a unit represented by the following chemical formula (27). Also, $^{13}$C-NMR confirmed the presence of unit C (3-hydroxy-6-bromohexanoic acid unit) and unit D (3-hydroxy-8-bromooctaonic acid unit), but the ratio of the unit C and the unit D was unknown.

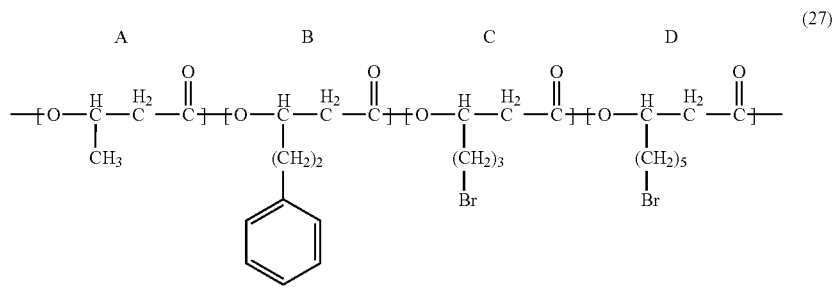

(27)

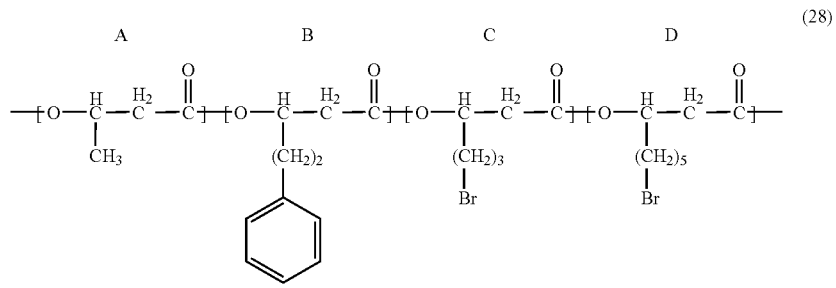

(28)

The molecular weight of the polymer was measured by GPC as in Example 1.

Table 7 shows weights of cells and the polymer, a polymer weight ratio to cells, a molecular weight and a molecular weight distribution of the obtained polymer.

TABLE 7

| CDW (mg/L) | PDW (mg/L) | P/C % | Mn × $10^4$ | Mw × $10^4$ | Mw/Mn |
|---|---|---|---|---|---|
| 556 | 173 | 31.1 | 3.4 | 7.1 | 2.1 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 8

A process was executed in the same manner as in Example 1, except that the polypeptone in the culture medium was changed to sodium glutamate, to obtain a desired polymer. A structure determination of the obtained polymer by $^1$H-NMR and $^{13}$C-NMR as in Example 1 confirmed a polyhydroxyalkanoate copolymer (A:B:C+D=1:91:8) containing a unit represented by the following chemical formula (29). Also, $^{13}$C-NMR confirmed the presence of unit C (3-hydroxy-6-bromohexanoic acid unit) and unit D (3-hydroxy-8-bromooctaonic acid unit), but the ratio of the unit C and the unit D was unknown.

TABLE 8

| CDW (mg/L) | PDW (mg/L) | P/C % | Mn × $10^4$ | Mw × $10^4$ | Mw/Mn |
|---|---|---|---|---|---|
| 479 | 169 | 35.3 | 3.5 | 7.2 | 2.1 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 9

125 g of polypeptone (supplied by Wako Pure Chemical Co.), 26.7 g of 5-phenylvaleric acid and 19.9 g of 11-bromoundecanoic acid were dissolved in 25 L of the aforementioned M9 culture medium, which was then charged in a 50 L jar fermenter, sterilized for 10 minutes at 121° C. and cooled to 30° C. To thus prepared culture medium, 200 ml of a culture liquid of Pseudomonas jessenii P161 strain, which was cultured with shaking in advance for 8 hours at 30° C. in an M9 culture medium containing 0.5% of polypeptone, was added and culturing was performed for 16 hours at 30° C., 70 rpm and an aeration rate of 9.4 L/min. After the culturing, bacteria cells were harvested by centrifuging, then washed with methanol and dried under a reduced pressure. After a weight measurement of the bacteria cells, 200 ml of chloroform was added and stirring was conducted for 16 hours at 35° C. to extract the polymer. The chloroform containing the extracted polymer was filtered, then concentrated with an evaporator, and a portion precipitated and solidified by cold methanol was collected and dried under a reduced pressure to obtain the desired polymer.

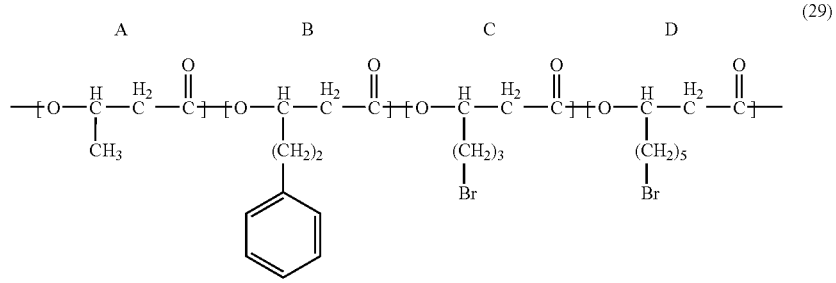

(29)

The molecular weight of the polymer was measured by GPC as in Example 1.

Table 8 shows weights of cells and the polymer, a polymer weight ratio to cells, a molecular weight and a molecular weight distribution of the obtained polymer.

A structure determination of the obtained polymer by $^1$H-NMR (FT-NMR:Bruker DPX400, 1H resonance frequency:400 MHz, measured nucleus species:1H, solvent: CDCl$_3$, reference:capillary-sealed TMS/CDCl$_3$, measurement temperature:room temperature) confirmed a polyhydroxyalkanoate copolymer (A:B:C=5:85:10) containing a unit represented by the following chemical formula (30).

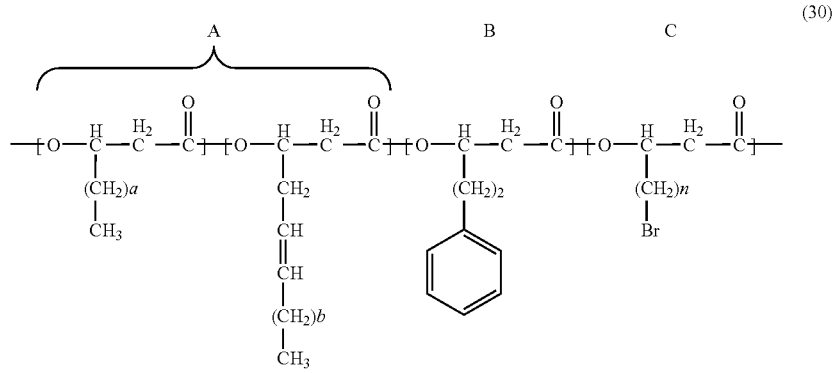

wherein a represents at least any integer from 0 to 10, b represents at least either one of integers 3 and 5, and n represents at least any one of integers 4, 6 and 8.

The molecular weight of the polymer was measured by gel permeation chromatography (GPC) (Tosoh HLC-8220, column: Tosoh TSK-GEL Super HM-H, solvent: chloroform, conversion to polystyrene).

Table 9 shows weights of cells and the polymer, a polymer weight ratio to cells, a molecular weight and a molecular weight distribution of the obtained polymer.

TABLE 9

| CDW (mg/L) | PDW (mg/L) | P/C % | Mn × $10^4$ | Mw × $10^4$ | Mw/Mn |
|---|---|---|---|---|---|
| 375 | 77 | 20.6 | 3.1 | 5.9 | 1.9 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 10

125 g of polypeptone (supplied by Wako Pure Chemical Co.), 29.1 g of 5-phenoxyvaleric acid and 5.6 g of 8-bromooctanoic acid were dissolved in 25 L of the aforementioned M9 culture medium, which was then charged in a 50 L jar fermenter, sterilized for 10 minutes at 121° C. and cooled to 30° C. To thus prepared culture medium, 200 ml of a culture liquid of *Pseudomonas cichorii* YN2 strain, which was cultured with shaking in advance for 8 hours at 30° C. in an M9 culture medium containing 0.5% of polypeptone, was added and the culture was performed for 15 hours at 30° C., 70 rpm and an aeration rate of 9.4 L/min. After the culture, bacteria cells were harvested by centrifuging, then washed with methanol and dried under a reduced pressure. After a weight measurement of the bacteria cells, 250 ml of chloroform was added and stirring was conducted for 42 hours at 35° C. to extract the polymer. The chloroform containing the extracted polymer was filtered, then concentrated with an evaporator, and a portion precipitated and solidified by cold methanol was collected and dried under a reduced pressure to obtain the desired polymer.

A structure determination of the obtained polymer by $^1$H-NMR (FT-NMR:Bruker DPX400, 1H resonance frequency:400 MHz, measured nucleus species:1H, solvent: $CDCl_3$, reference:capillary-sealed TMS/$CDCl_3$, measurement temperature:room temperature) confirmed a polyhydroxyalkanoate copolymer (E:F:G=6:87:7) containing a unit represented by the following chemical formula (31).

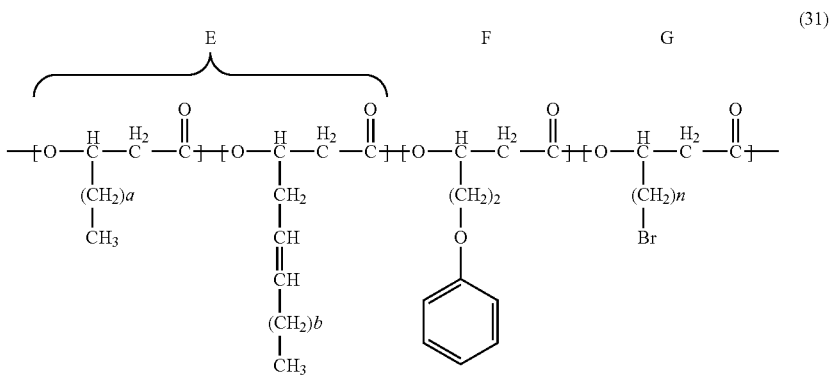

wherein a represents at least any integer from 1 to 10, b represents at least either one of integers 3 and 5, and n represents at least any one of integers 3 and 5.

The molecular weight of the polymer was measured by gel permeation chromatography (GPC) (Tosoh HLC-8220, column: Tosoh TSK-GEL Super HM-H, solvent: chloroform, conversion to polystyrene).

Figure 3:
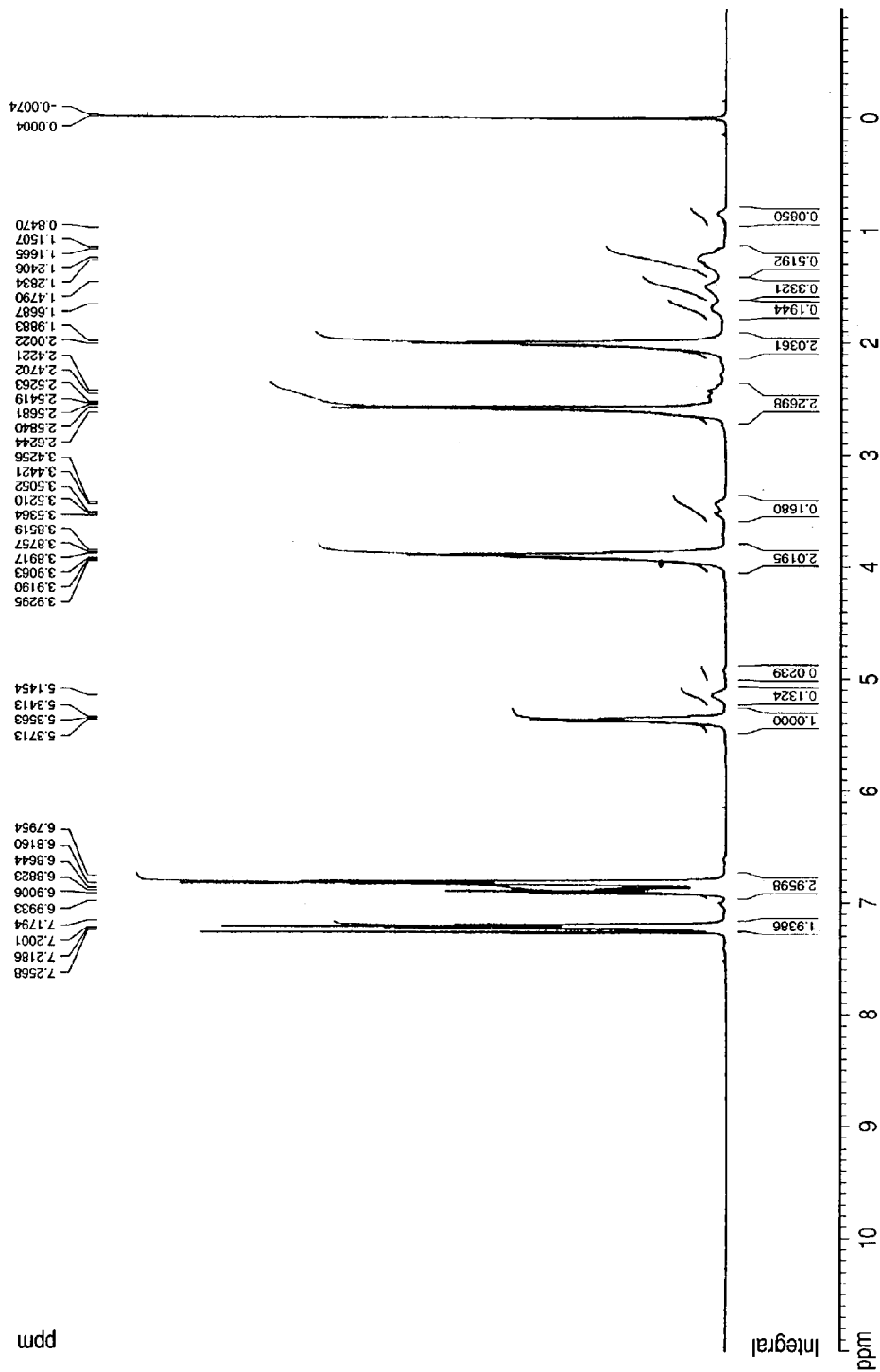
FIG. 3 is a chart showing the $^1$H-NMR spectrum of a polyester obtained in Example 10.

FIG. 3 shows the $^1$H-NMR spectrum of the obtained polymer. Also, Table 10 shows weights of cells and the polymer, a polymer weight ratio to cells, a molecular weight and a molecular weight distribution of the obtained polymer.

TABLE 10

| CDW (mg/L) | PDW (mg/L) | P/C % | Mn × 10$^4$ | Mw × 10$^4$ | Mw/Mn |
|---|---|---|---|---|---|
| 402 | 33 | 8.2 | 3.1 | 6.5 | 2.1 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 11

1.0 g of polypeptone (supplied by Wako Pure Chemical Co.), 0.23 g of 5-phenoxyvaleric acid and 0.004 g of 8-bromooctanoic acid were dissolved in 200 ml of the aforementioned M9 culture medium, which was then charged in a 500 ml shaking flask, sterilized in an autoclave and cooled to room temperature. To thus prepared culture medium, 2.0 ml of a culture liquid of *Pseudomonas cichorii* YN2 strain, which was cultured with shaking in advance for 8 hours at 30° C. in an M9 culture medium containing 0.5% of polypeptone, was added and the culture was performed for 65 hours at 30° C. After the culture, bacteria cells were harvested by centrifuging, then washed with methanol and dried under a reduced pressure. After a weight measurement of the bacteria cells, 20 ml of chloroform was added and stirring was conducted for 63 hours at 35° C. to extract the polymer. The chloroform containing the extracted polymer was filtered, then concentrated with an evaporator, and a portion precipitated and solidified by cold methanol was collected and dried under a reduced pressure to obtain the desired polymer.

A structure determination of the obtained polymer by $^1$H-NMR (FT-NMR:Bruker DPX400, 1H resonance frequency:400 MHz, measured nucleus species:1H, solvent: CDCl$_3$, reference:capillary-sealed TMS/CDCl$_3$, measurement temperature:room temperature) confirmed a polyhydroxyalkanoate copolymer (E:F:G=6:91:3) containing a unit represented by the following chemical formula (32).

wherein a represents at least any one of integers from 1 to 10, b represents at least either one of integers 3 and 5, and n represents at least any one of integers 3 and 5.

The molecular weight of the polymer was measured by gel permeation chromatography (GPC) (Tosoh HLC-8220, column: Tosoh TSK-GEL Super HM-H, solvent: chloroform, conversion to polystyrene).

Table 11 shows weights of cells and the polymer, a polymer weight ratio to cells, a molecular weight and a molecular weight distribution of the obtained polymer.

TABLE 11

| CDW (mg/L) | PDW (mg/L) | P/C % | Mn × 10$^4$ | Mw × 10$^4$ | Mw/Mn |
|---|---|---|---|---|---|
| 502 | 203 | 40.4 | 8.0 | 17.0 | 2.1 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 12

1.0 g of D-glucose, 0.23 g of 5-phenoxyvaleric acid and 0.13 g of 8-bromooctanoic acid were dissolved in 200 ml of the aforementioned M9 culture medium, which was then charged in a 500 ml shaking flask, sterilized in an autoclave and cooled to room temperature (culture medium 1). Next, 1.0 g of D-glucose, 0.23 g of 5-phenoxyvaleric acid and 0.13 g of 8-bromooctanoic acid were dissolved in 200 ml of a culture medium formed by eliminating only the nitrogen source (NH$_4$Cl) from the aforementioned M9 culture medium, which was then charged in a 500 ml shaking flask, sterilized in an autoclave and cooled to room temperature (culture medium 2).

To the culture medium 1, 2.0 ml of a culture liquid of *Pseudomonas cichorii* YN2 strain, which was cultured with shaking in advance for 8 hours at 30° C. in an M9 culture medium containing 0.5% of polypeptone, was added and the culture was performed for 40 hours at 30° C. After the culture, bacteria cells were harvested by centrifuging, suspended in the culture medium 2 and subjected to a vibration culture for 98 hours at 30° C. After the culture, the bacteria cells were harvested by centrifuging, then washed with methanol and dried under a reduced pressure. After a weight measurement of the dried bacteria cells, 20 ml of chloroform was added and stirring was conducted for 63 hours at 35° C. to extract the polymer. The chloroform containing the extracted polymer was filtered, then concentrated with an evaporator, and a portion precipitated and solidified by cold methanol was collected and dried under a reduced pressure to obtain the desired polymer.

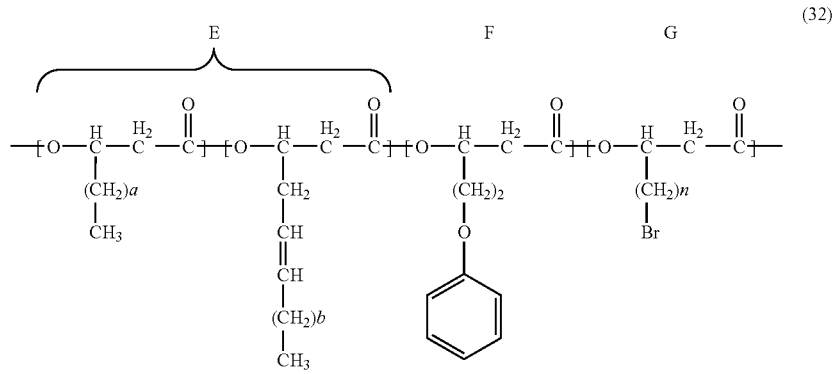

(32)

A structure determination of the obtained polymer by $^1$H-NMR (FT-NMR:Bruker DPX400, 1H resonance frequency:400 MHz, measured nucleus species:1H, solvent: $CDCl_3$, reference:capillary-sealed $TMS/CDCl_3$, measurement temperature:room temperature) confirmed a polyhydroxyalkanoate copolymer (E:F:G=22:58:20) containing a unit represented by the following chemical formula (33).

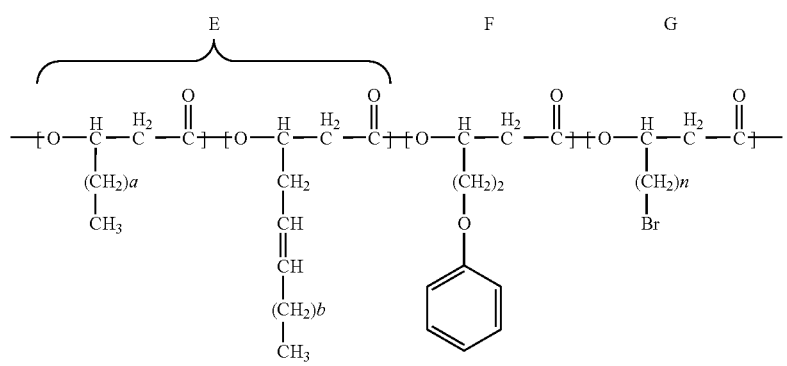

(33)

wherein a represents at least any of integers from 1 to 10, b represents at least either of integers 3 and 5, and n represents at least any of integers 3 and 5.

The molecular weight of the polymer was measured by gel permeation chromatography (GPC) (Tosoh HLC-8220, column: Tosoh TSK-GEL Super HM-H, solvent: chloroform, conversion to polystyrene).

Table 12 shows weights of cells and the polymer, a polymer weight ratio to cells, a molecular weight and a molecular weight distribution of the obtained polymer.

TABLE 12

| CDW (mg/L) | PDW (mg/L) | P/C % | $Mn \times 10^4$ | $Mw \times 10^4$ | Mw/Mn |
|---|---|---|---|---|---|
| 431 | 52 | 12.1 | 3.1 | 6.7 | 2.2 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

charged in a 2,000 ml shaking flask, sterilized in an autoclave and cooled to room temperature. To thus prepared culture medium, 10 ml of a culture liquid of *Pseudomonas cichorii* YN2 strain, which was cultured with shaking in advance for 8 hours at 30° C. in an M9 culture medium containing 0.5% of polypeptone, was added and a vibration culture was executed for 17 hours at 30° C.

After the culture, bacteria cells were harvested by centrifuging, then washed with methanol and dried under a reduced pressure. After a weight measurement of the bacteria cells, 50 ml of chloroform was added and stirring was conducted for 45 hours at 35° C. to extract the polymer. The chloroform containing the extracted polymer was filtered, then concentrated with an evaporator, and a portion precipitated and solidified by cold methanol was collected and dried under a reduced pressure to obtain the desired polymer.

A structure determination of the obtained polymer by $^1$H-NMR (FT-NMR:Bruker DPX400, 1H resonance frequency:400 MHz, measured nucleus species:1H, solvent: $CDCl_3$, reference:capillary-sealed $TMS/CDCl_3$, measurement temperature:room temperature) confirmed a polyhydroxyalkanoate copolymer (E:F:G=14:79:7) containing a unit represented by the following chemical formula (34).

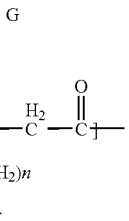

(34)

Example 13

5.0 g of polypeptone (supplied by Wako Pure Chemical Co.), 1.2 g of 5-phenoxyvaleric acid and 0.3 g of 11-bromoundecanoic acid were dissolved in 1,000 ml of the aforementioned M9 culture medium, which was then wherein a represents at least any one of integers from 1 to 10, b represents at least either one of integers 3 and 5, and n represents at least any one of integers 4, 6 and 8.

The molecular weight of the polymer was measured by gel permeation chromatography (GPC) (Tosoh HLC-8220, column: Tosoh TSK-GEL Super HM-H, solvent: chloroform, conversion to polystyrene).

Figure 4:
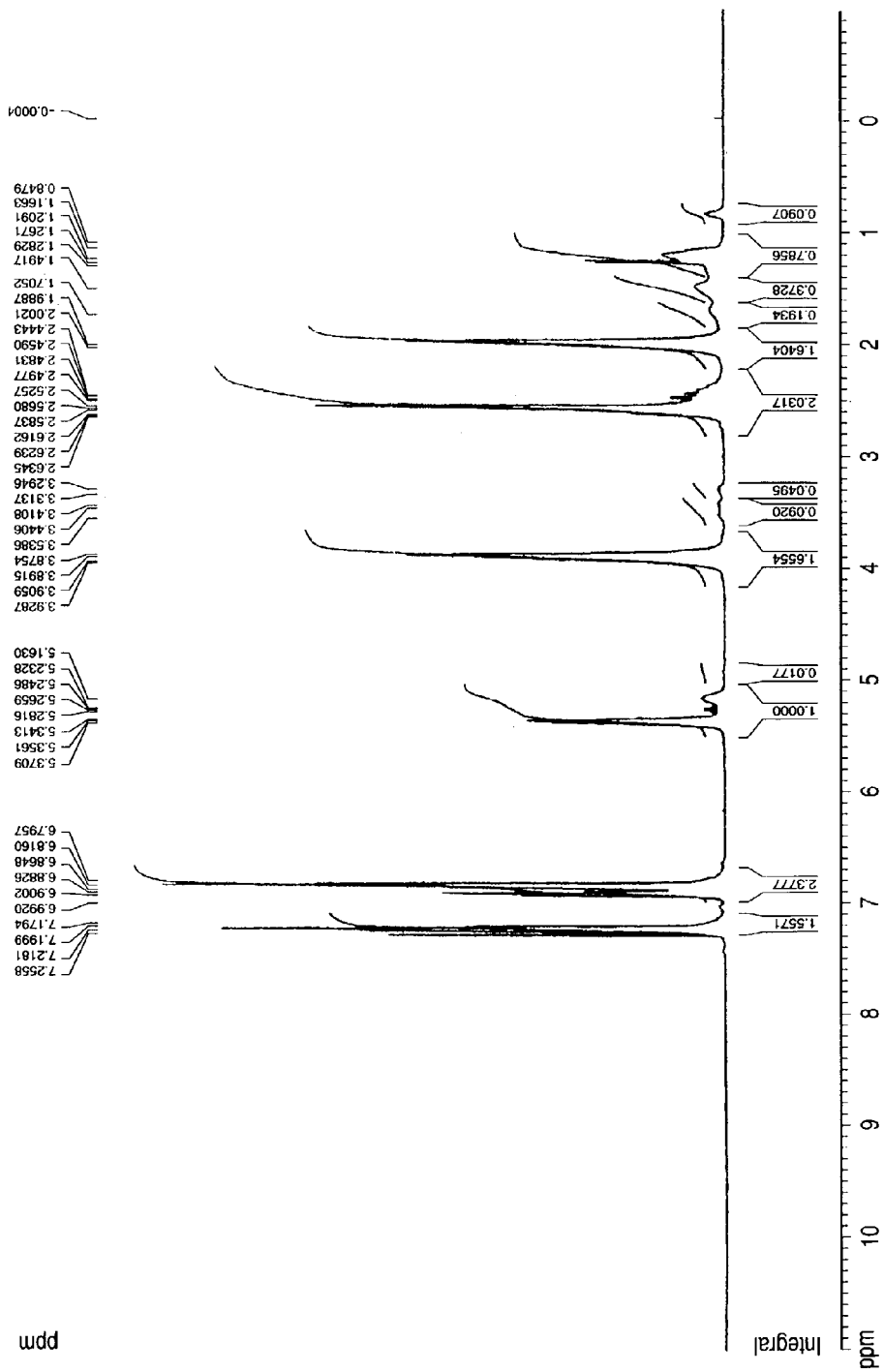
FIG. 4 is a chart showing the $^1$H-NMR spectrum of a polyester obtained in Example 13.

FIG. 4 shows the $^1$H-NMR spectrum of the obtained polymer. Also, Table 13 shows weights of cells and the polymer, a polymer weight ratio to cells, a molecular weight and a molecular weight distribution of the obtained polymer.

TABLE 13

| CDW (mg/L) | PDW (mg/L) | P/C % | Mn × 10$^4$ | Mw × 10$^4$ | Mw/Mn |
|---|---|---|---|---|---|
| 743 | 82 | 11.0 | 4.8 | 11.0 | 2.3 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 14

1.0 g of polypeptone (supplied by Wako Pure Chemical Co.), 0.23 g of 5-phenoxyvaleric acid and 0.05 g of 11-bromoundecanoic acid were dissolved in 200 ml of the aforementioned M9 culture medium, which was then charged in a 500 ml shaking flask, sterilized in an autoclave and cooled to room temperature. To thus prepared culture medium, 2.0 ml of a culture liquid of *Pseudomonas cichorii* YN2 strain, which was cultured with shaking in advance for 8 hours at 30° C. in an M9 culture medium containing 0.5% of polypeptone, was added and a vibration culture was executed for 67 hours at 30° C. After the culture, bacteria cells were harvested by centrifuging, then washed with methanol and dried under a reduced pressure. After a weight measurement of the bacteria cells, 20 ml of chloroform was added and stirring was conducted for 64 hours at 35° C. to extract the polymer. The chloroform containing the extracted polymer was filtered, then concentrated with an evaporator, and a portion precipitated and solidified by cold methanol was collected and dried under a reduced pressure to obtain the desired polymer.

A structure determination of the obtained polymer by $^1$H-NMR (FT-NMR:Bruker DPX400, 1H resonance frequency:400 MHz, measured nucleus species:1H, solvent: CDCl$_3$, reference:capillary-sealed TMS/CDCl$_3$, measurement temperature:room temperature) confirmed a polyhydroxyalkanoate copolymer (E:F:G=5:86:9) containing a unit represented by the following chemical formula (35).

wherein a represents at least any one of integers from 1 to 10, b represents at least either one of integers 3 and 5, and n represents at least any one of integers 4, 6 and 8.

The molecular weight of the polymer was measured by gel permeation chromatography (GPC) (Tosoh HLC-8220, column: Tosoh TSK-GEL Super HM-H, solvent: chloroform, conversion to polystyrene).

Table 14 shows weights of cells and the polymer, a polymer weight ratio to cells, a molecular weight and a molecular weight distribution of the obtained polymer.

TABLE 14

| CDW (mg/L) | PDW (mg/L) | P/C % | Mn × 10$^4$ | Mw × 10$^4$ | Mw/Mn |
|---|---|---|---|---|---|
| 500 | 29 | 5.8 | 5.9 | 14.0 | 2.4 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 15

1.0 g of polypeptone (supplied by Wako Pure Chemical Co.), 0.12 g of 5-phenoxyvaleric acid and 0.05 g of 11-bromoundecanoic acid were dissolved in 200 ml of the aforementioned M9 culture medium, which was then charged in a 500 ml shaking flask, sterilized in an autoclave and cooled to room temperature. To thus prepared culture medium, 2.0 ml of a culture liquid of *Pseudomonas cichorii* YN2 strain, which was cultured with shaking in advance for 8 hours at 30° C. in an M9 culture medium containing 0.5% of polypeptone, was added and a vibration culture was executed for 67 hours at 30° C. After the culture, bacteria cells were harvested by centrifuging, then washed with methanol and dried under a reduced pressure. After a weight measurement of the dried bacteria cells, 20 ml of chloroform was added and stirring was conducted for 64 hours at 35° C. to extract the polymer. The chloroform containing the extracted polymer was filtered, then concentrated with an evaporator, and a portion precipitated and solidified by cold methanol was collected and dried under a reduced pressure to obtain the desired polymer.

A structure determination of the obtained polymer by $^1$H-NMR (FT-NMR:Bruker DPX400, 1H resonance frequency:400 MHz, measured nucleus species:1H, solvent: CDCl$_3$, reference:capillary-sealed TMS/CDCl$_3$, measurement temperature:room temperature) confirmed a $$\overbrace{-\left[O-\underset{\underset{\underset{CH_3}{|}}{\underset{(CH_2)a}{|}}}{\overset{H}{C}}-\overset{H_2}{C}-\overset{O}{\overset{\|}{C}}\right]-\left[O-\underset{\underset{\underset{\underset{CH_3}{|}}{\underset{(CH_2)b}{|}}}{\underset{\underset{CH}{\|}}{\underset{CH}{|}}}}{\underset{CH_2}{|}}{\overset{H}{C}}-\overset{H_2}{C}-\overset{O}{\overset{\|}{C}}\right]}^{E}-\overset{F}{\left[O-\underset{\underset{\underset{\bigcirc}{|}}{\underset{O}{|}}}{\underset{(CH_2)_2}{|}}{\overset{H}{C}}-\overset{H_2}{C}-\overset{O}{\overset{\|}{C}}\right]}-\overset{G}{\left[O-\underset{\underset{Br}{|}}{\underset{(CH_2)n}{|}}{\overset{H}{C}}-\overset{H_2}{C}-\overset{O}{\overset{\|}{C}}\right]} \quad (35)$$

polyhydroxyalkanoate copolymer (E:F:G=13:76:11) containing a unit represented by the following chemical formula (36).

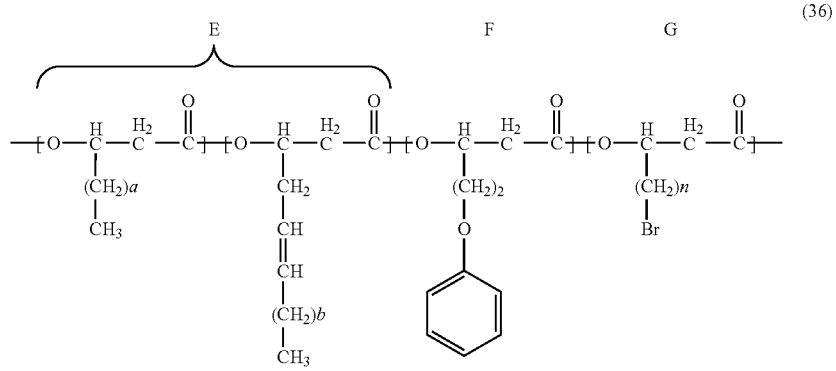

wherein a represents at least any one of integers from 1 to 10, b represents at least either one of integers 3 and 5, and n represents at least any one of integers 4, 6 and 8.

The molecular weight of the polymer was measured by gel permeation chromatography (GPC) (Tosoh HLC-8220, column: Tosoh TSK-GEL Super HM-H, solvent: chloroform, conversion to polystyrene).

Table 15 shows weights of cells and the polymer, a polymer weight ratio to cells, a molecular weight and a molecular weight distribution of the obtained polymer.

TABLE 15

| CDW (mg/L) | PDW (mg/L) | P/C % | Mn × $10^4$ | Mw × $10^4$ | Mw/Mn |
|---|---|---|---|---|---|
| 552 | 46 | 8.3 | 4.9 | 12.0 | 2.4 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 16

1.0 g of polypeptone (supplied by Wako Pure Chemical Co.), 0.25 g of 5-benzoylvaleric acid and 0.05 g of 11-bromoundecanoic acid were dissolved in 200 ml of the aforementioned M9 culture medium, which was then charged in a 500 ml shaking flask, sterilized in an autoclave and cooled to room temperature. To thus prepared culture medium, 2.0 ml of a culture liquid of *Pseudomonas cichorii* YN2 strain, which was cultured with shaking in advance for 8 hours at 30° C. in an M9 culture medium containing 0.5% of polypeptone, was added and a vibration culture was executed for 64 hours at 30° C. After the culture, bacteria cells were harvested by centrifuging, then washed with methanol and dried under a reduced pressure. After a weight measurement of the dried bacteria cells, 20 ml of chloroform was added and stirring was conducted for 48 hours at 35° C. to extract the polymer. The chloroform containing the extracted polymer was filtered, then concentrated with an evaporator, and a portion precipitated and solidified by cold methanol was collected and dried under a reduced pressure to obtain the desired polymer.

A structure determination of the obtained polymer by $^1$H-NMR (FT-NMR:Bruker DPX400, 1H resonance frequency:400 MHz, measured nucleus species:1H, solvent: $CDCl_3$, reference:capillary-sealed TMS/$CDCl_3$, measurement temperature:room temperature) confirmed a polyhydroxyalkanoate copolymer (H:I:J=11:80:9) containing a unit represented by the following chemical formula (37).

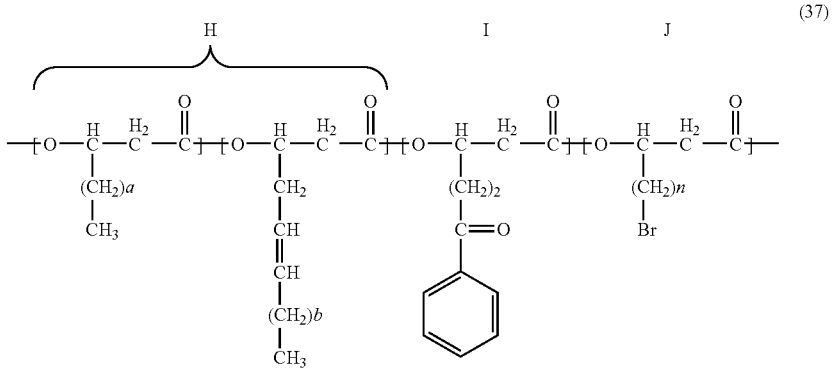

wherein a represents at least any one of integers from 1 to 10, b represents at least either one of integers 3 and 5, and n represents at least any one of integers 4, 6 and 8.

ment temperature:room temperature) confirmed a polyhydroxyalkanoate copolymer (K:L=88:12) containing a unit represented by the following chemical formula (38).

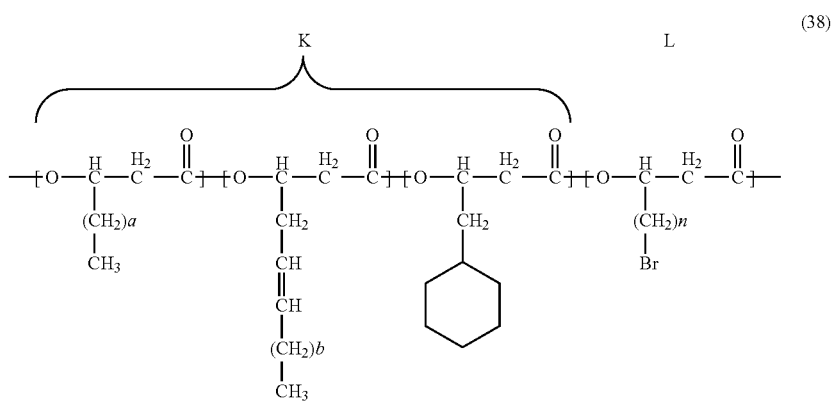

(38)

The molecular weight of the polymer was measured by gel permeation chromatography (GPC) (Tosoh HLC-8220, column: Tosoh TSK-GEL Super HM-H, solvent: chloroform, conversion to polystyrene).

Figure 5:
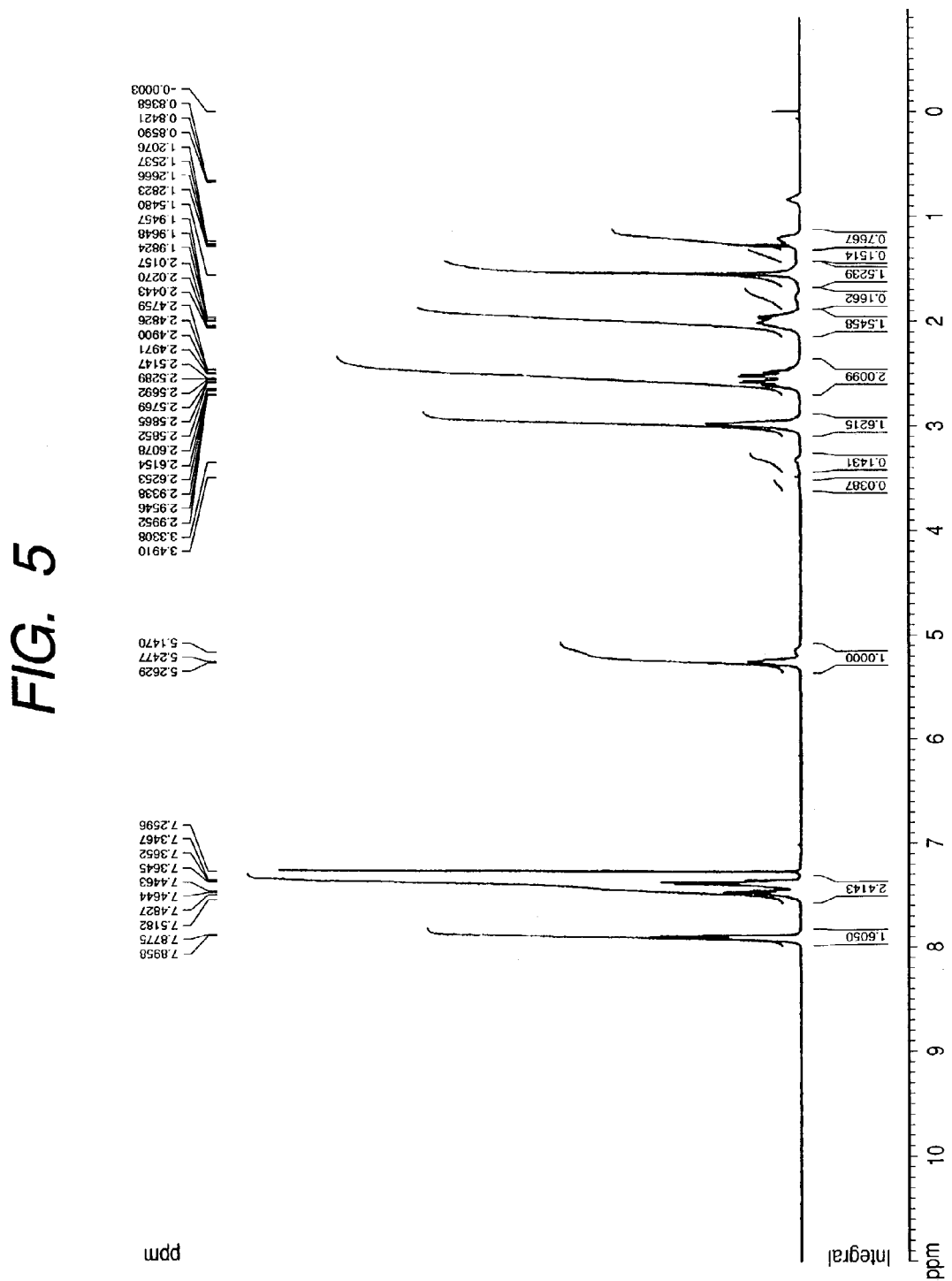
FIG. 5 is a chart showing the $^1$H-NMR spectrum of a polyester obtained in Example 16.

FIG. 5 shows the $^1$H-NMR spectrum of the obtained polymer. Also, Table 16 shows weights of cells and the polymer, a polymer weight ratio to cells, a molecular weight and a molecular weight distribution of the obtained polymer.

TABLE 16

| CDW (mg/L) | PDW (mg/L) | P/C % | Mn × $10^4$ | Mw × $10^4$ | Mw/Mn |
|---|---|---|---|---|---|
| 521 | 22 | 4.2 | 6.9 | 16.0 | 23 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 17

1.0 g of polypeptone (supplied by Wako Pure Chemical Co.), 0.20 g of 4-cyclohexylbutyric acid and 0.13 g of 8-bromooctanoic acid were dissolved in 200 ml of the aforementioned M9 culture medium, which was then charged in a 500 ml shaking flask, sterilized in an autoclave and cooled to room temperature. To thus prepared culture medium, 2.0 ml of a culture liquid of *Pseudomonas cichorii* YN2 strain, which was cultured with shaking in advance for 8 hours at 30° C. in an M9 culture medium containing 0.5% of polypeptone, was added and a vibration culture was executed for 40 hours at 30° C. After the culture, bacteria cells were harvested by centrifuging, then washed with methanol and dried under a reduced pressure. After a weight measurement of the dried bacteria cells, 20 ml of chloroform was added and stirring was conducted for 17 hours at 35° C. to extract the polymer. The chloroform containing the extracted polymer was filtered, then concentrated with an evaporator, and a portion precipitated and solidified by cold methanol was collected and dried under a reduced pressure to obtain the desired polymer.

A structure determination of the obtained polymer by $^1$H-NMR (FT-NMR:Bruker DPX400, 1H resonance frequency:400 MHz, measured nucleus species:1H, solvent: CDCl$_3$, reference:capillary-sealed TMS/CDCl$_3$, measurewherein a represents at least any one of integers from 1 to 10, b represents at least either one of integers 3 and 5, and n represents at least any one of integers 3 and 5.

The molecular weight of the polymer was measured by gel permeation chromatography (GPC) (Tosoh HLC-8220, column: Tosoh TSK-GEL Super HM-H, solvent: chloroform, conversion to polystyrene).

Figure 6:
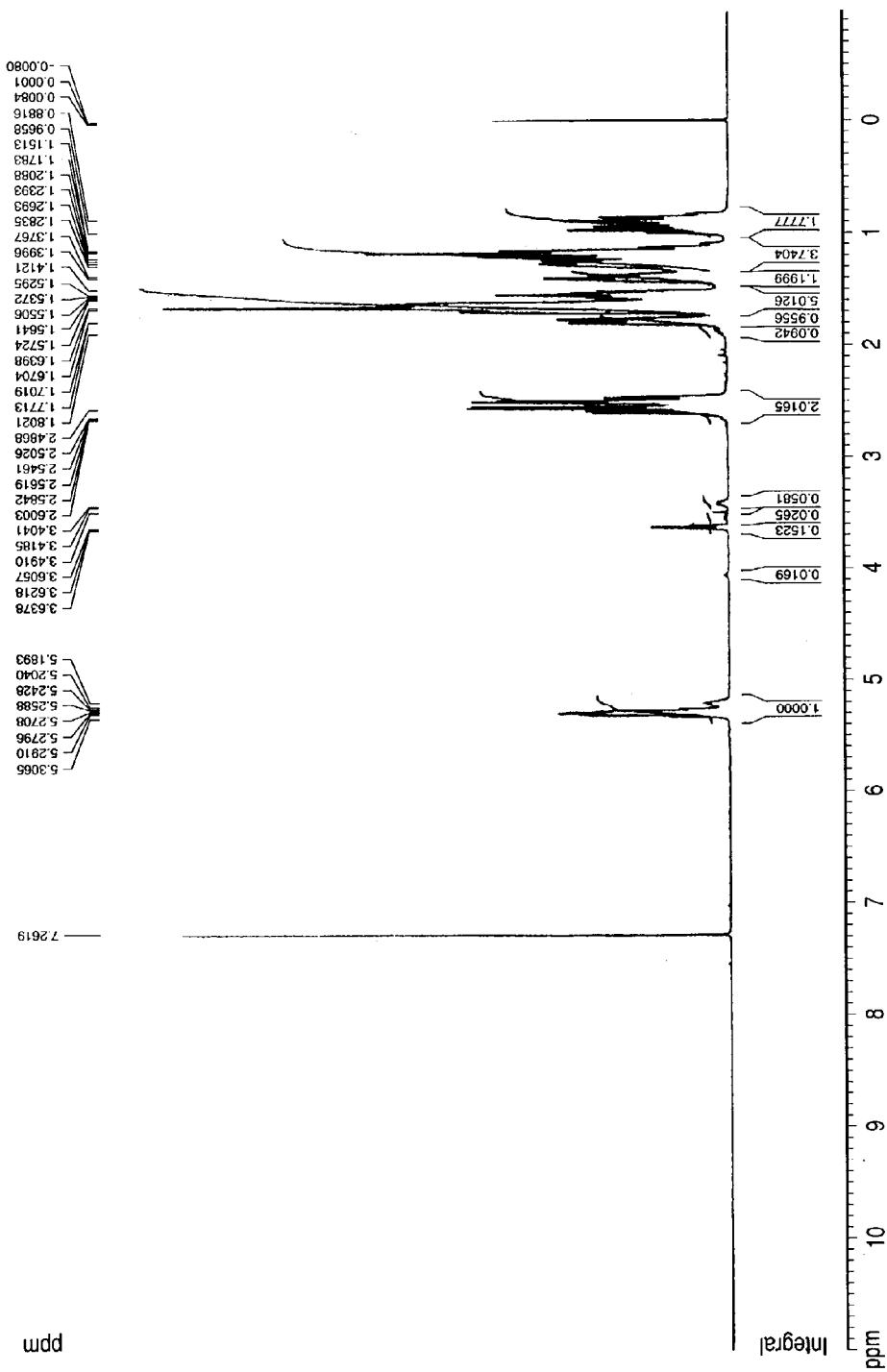
FIG. 6 is a chart showing the $^1$H-NMR spectrum of a polyester obtained in Example 17.

FIG. 6 shows the $^1$H-NMR spectrum of the obtained polymer. Also, Table 17 shows weights of cells and the polymer, a polymer weight ratio to cells, a molecular weight and a molecular weight distribution of the obtained polymer.

TABLE 17

| CDW (mg/L) | PDW (mg/L) | P/C % | Mn × $10^4$ | Mw × $10^4$ | Mw/Mn |
|---|---|---|---|---|---|
| 945 | 242 | 25.6 | 4.0 | 11.0 | 2.8 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 18

1.0 g of polypeptone (supplied by Wako Pure Chemical Co.), 1.28 g of 5-(phenylsulfanyl)valeric acid and 0.80 g of 11-bromoundecanoic acid were dissolved in 1.0 L of the aforementioned M9 culture medium, which was then charged in a 2.0 L shaking flask, sterilized in an autoclave and cooled to room temperature. To thus prepared culture medium, 10.0 ml of a culture liquid of *Pseudomonas cichorii* YN2 strain, which was cultured with shaking in advance for 8 hours at 30° C. in an M9 culture medium containing 0.5% of polypeptone, was added and a vibration culture was executed for 16 hours at 30° C. After the culture, bacteria cells were harvested by centrifuging, then washed with methanol and dried under a reduced pressure. After a weight measurement of the dried bacteria cells, 100 ml of chloroform was added and stirring was conducted for 18 hours at 35° C. to extract the polymer. The chloroform containing the extracted polymer was filtered, then concentrated with an evaporator, and a portion precipitated and solidified by cold methanol was collected and dried under a reduced pressure to obtain the desired polymer.

A structure determination of the obtained polymer by ¹H-NMR (FT-NMR:Bruker DPX400, 1H resonance frequency:400 MHz, measured nucleus species:1H, solvent: CDCl₃, reference:capillary-sealed TMS/CDCl₃, measurement temperature:room temperature) confirmed a polyhydroxyalkanoate copolymer (M:N:O=4:86:10) containing a unit represented by the following chemical formula (39).

11-bromoundecanoic acid were dissolved in 25 L of the aforementioned M9 culture medium, which was then charged in a 50 L jar fermenter, sterilized for 10 minutes at 121° C. and cooled to 30° C. To thus prepared culture medium, 200 ml of a culture liquid of *Pseudomonas cichorii* YN2 strain, which was cultured with shaking in advance for 8 hours at 30° C. in an M9 culture medium containing 0.5% of polypeptone, was added and the culture was performed

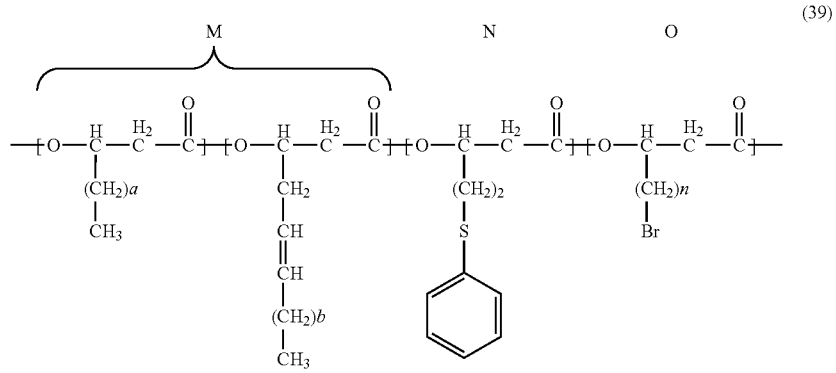

wherein a represents at least any one of integers from 1 to 10, b represents at least either one of integers 3 and 5, and n represents at least any one of integers 4, 6 and 8.

Figure 7:
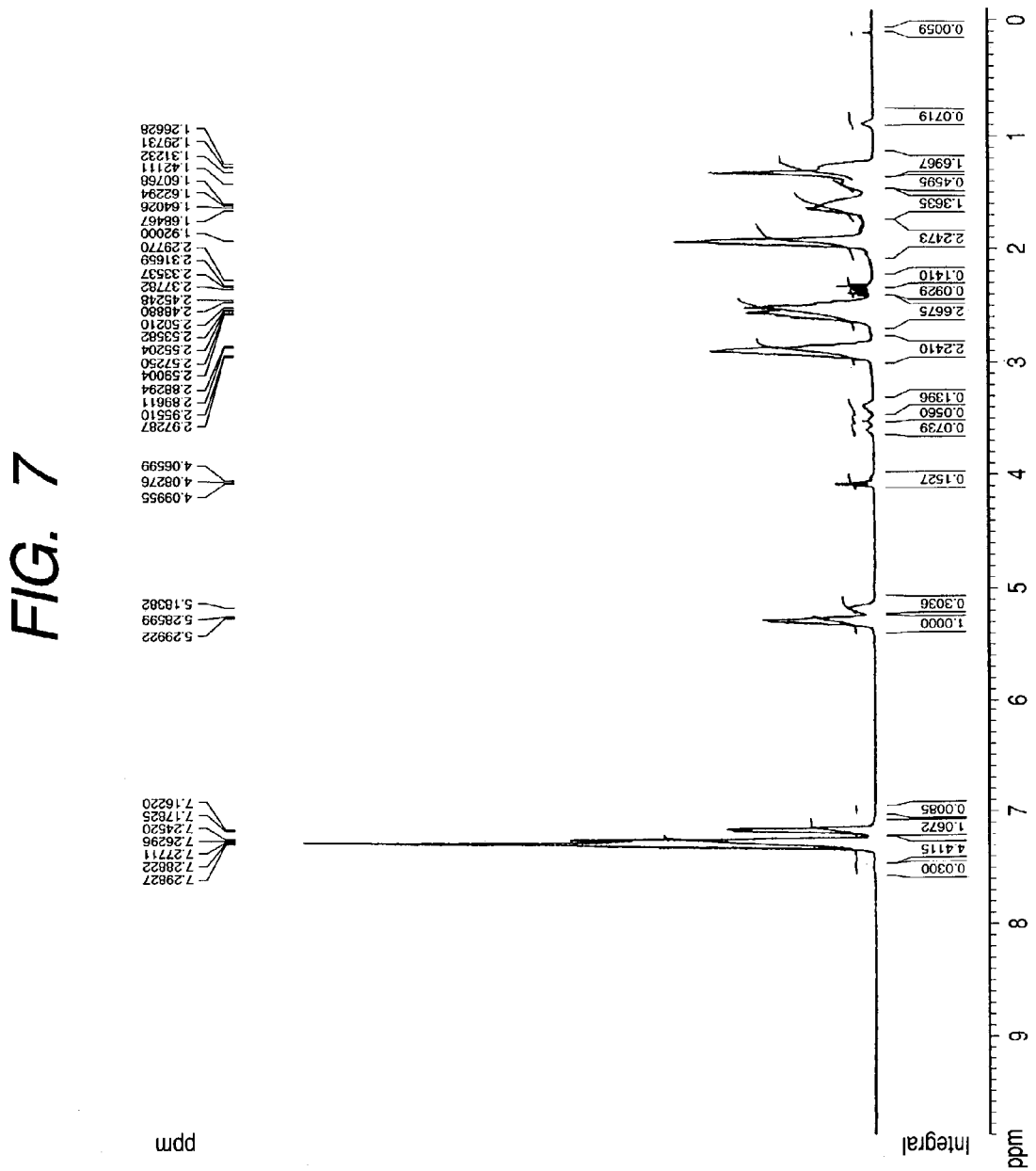
FIG. 7 is a chart showing the $^1$H-NMR spectrum of a polyester obtained in an example 18.
Figure 8:
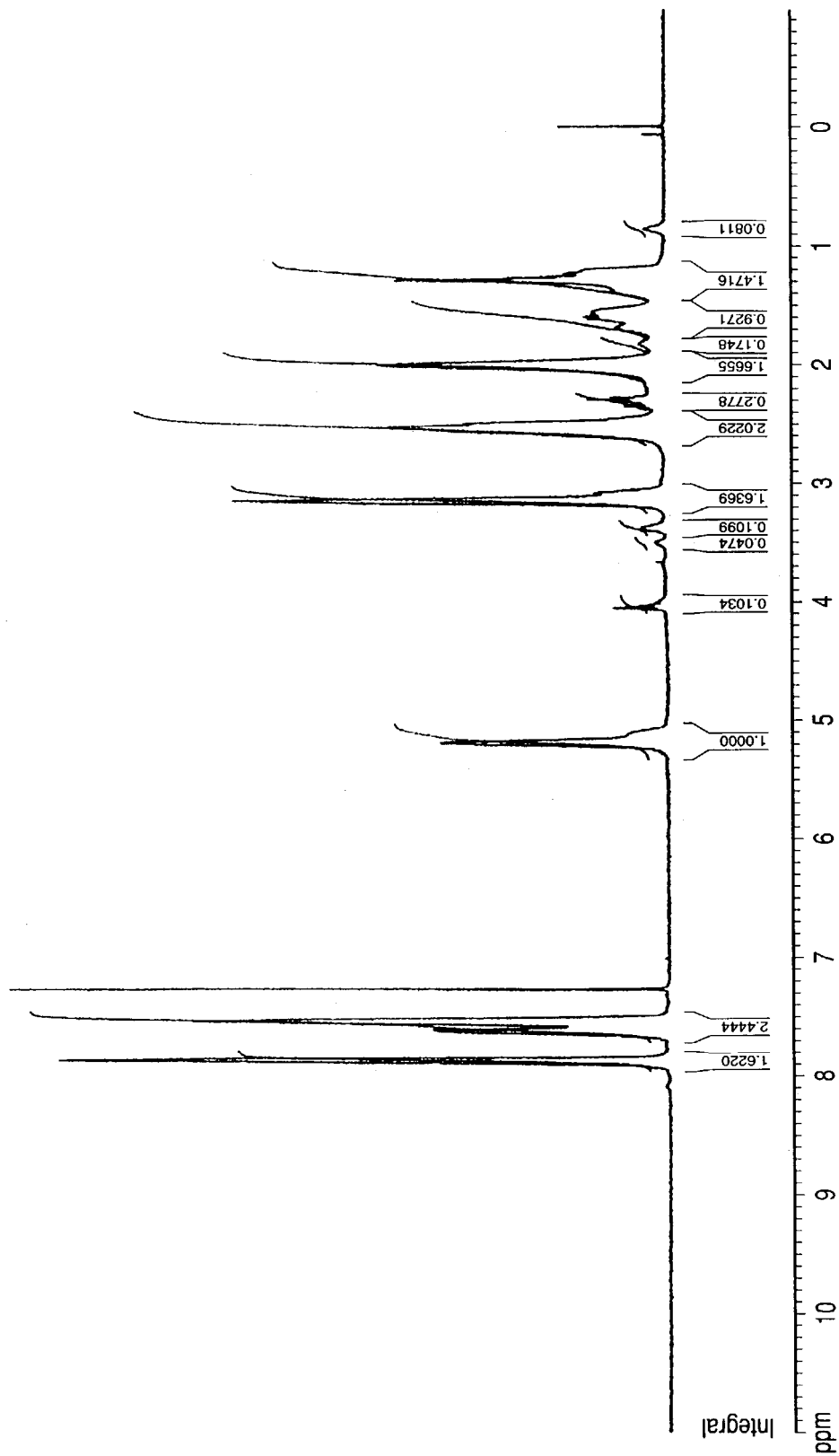
FIG. 8 is a chart showing the $^1$H-NMR spectrum of a polyester obtained in Example 20.

FIG. 7 shows the ¹H-NMR spectrum of the obtained polymer. Also, Table 18 shows weights of cells and the polymer, and a polymer weight ratio to cells.

TABLE 18

| CDW (mg/L) | PDW (mg/L) | P/C % |
|---|---|---|
| 727 | 127 | 17.4 |

CDW: cell dry weight,
PDW: polymer dry weight,
P/C: polymer dry weight/cell dry weight.

Example 19

125 g of polypeptone (supplied by Wako Pure Chemical Co.), 32.1 g of 5-(phenylsulfanyl)valeric acid and 19.9 g of for 16 hours at 30° C., 70 rpm and an aeration rate of 9.4 L/min. After the culture, bacteria cells were harvested by centrifuging, then washed with methanol and dried under a reduced pressure. After a weight measurement of the dried bacteria cells, 150 ml of chloroform was added and stirring was conducted for 13 hours at 35° C. to extract the polymer. The chloroform containing the extracted polymer was filtered, then concentrated with an evaporator, and a portion precipitated and solidified by cold methanol was collected and dried under a reduced pressure to obtain the desired polymer.

A structure determination of the obtained polymer by ¹H-NMR (FT-NMR:Bruker DPX400, 1H resonance frequency:400 MHz, measured nucleus species:1H, solvent: CDCl₃, reference:capillary-sealed TMS/CDCl₃, measurement temperature:room temperature) confirmed a polyhydroxyalkanoate copolymer (M:N:O=17:63:20) containing a unit represented by the following chemical formula (40).

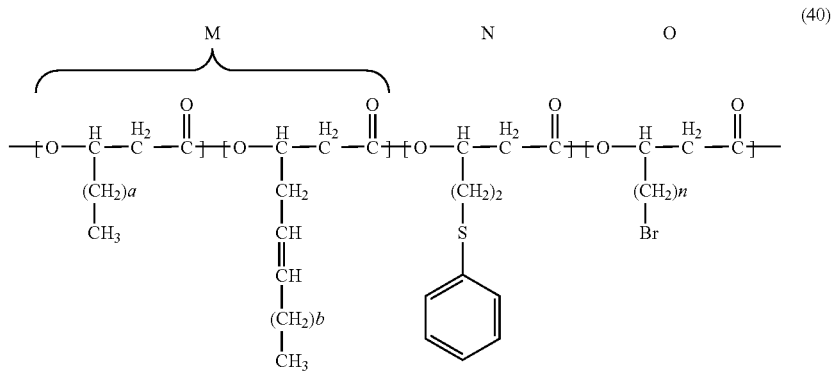

wherein a represents at least any one of integers from 0 to 10, b represents at least either one of integers 3 and 5, and n represents at least any one of integers 4, 6 and 8.

The molecular weight of the polymer was measured by gel permeation chromatography (GPC) (Tosoh HLC-8220, column: Tosoh TSK-GEL Super HM-H, solvent: chloroform, conversion to polystyrene).

Table 19 shows weights of cells and the polymer, a polymer weight ratio to cells, a molecular weight and a molecular weight distribution of the obtained polymer.

TABLE 19

| CDW (mg/L) | PDW (mg/L) | P/C % | $Mn \times 10^4$ | $Mw \times 10^4$ | Mw/Mn |
|---|---|---|---|---|---|
| 314 | 42 | 13.3 | 2.1 | 4.5 | 2.1 |

CDW: cell dry weight, PDW: polymer dry weight, P/C: polymer dry weight/cell dry weight, Mn: number-average molecular weight, Mw: weight-average molecular weight, Mw/Mn: molecular weight distribution.

Example 20

300 mg of the polymer obtained in Example 18 were charged in a 300 ml flask, and were dissolved by adding 30 ml of dichloromethane. The solution was placed on an ice bath and agitated with an addition of 6 ml of acetic acid and 1001 mg of 18-crown-6-ether. Then, 798 mg of potassium permanganate was slowly added to the solution on the ice bath and stirring was conducted for 21 hours at the room temperature. After the reaction, 50 ml of water and 1000 mg of sodium hydrogensulfite were added. Then, pH of the liquid was brought to pH 1 with 1.0 mol/L (1.0 N) hydrochloric acid. Dichloromethane in the mixed solution was distilled off by an evaporator to recover the polymer in the solution. The polymer was washed with 200 ml of methanol, then washed three times with 200 ml of purified water and dried under a reduced pressure to obtain 313 mg of polymer.

A structure determination of the obtained polymer by $^1$H-NMR (FT-NMR:Bruker DPX400, 1H resonance frequency:400 MHz, measured nucleus species:1H, solvent: CDCl$_3$, reference:capillary-sealed TMS/CDCl$_3$, measurement temperature:room temperature) confirmed a polyhydroxyalkanoate copolymer (P:Q:R=11:81:8) containing a unit represented by the following chemical formula (41).

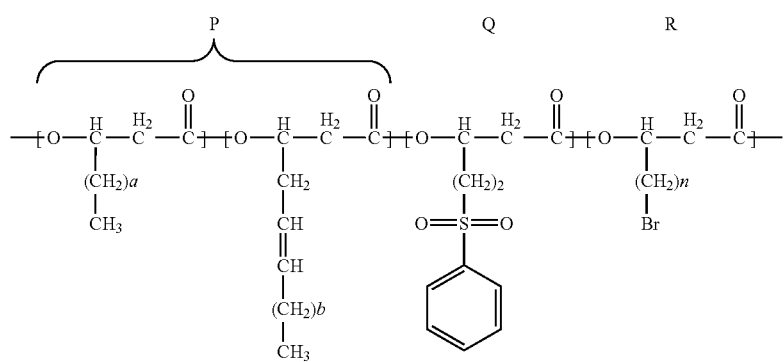

(41)

wherein a represents at least any one of integers from 0 to 10, b represents at least either one of integers 3 and 5, and n represents at least any one of integers 4, 6 and 8.

The molecular weight of the polymer was measured by gel permeation chromatography (GPC) (Tosoh HLC-8220, column: Tosoh TSK-GEL Super HM-H, solvent: chloroform, conversion to polystyrene). As a result, the number-average molecular weight Mn was 13300.

As explained in the foregoing, the present invention provides a novel polyhydroxyalkanoate copolymer including a unit having a bromo group in a side chain and a unit having a residue including a phenyl, thiophene or cyclohexyl structure in a side chain, within the same molecule, and a producing method therefor.

The invention claimed is:

1. A polyhydroxyalkanoate copolymer comprising a 3-hydroxy-ω-bromoalkanoic acid unit represented by a chemical formula (1) and a unit represented by a chemical formula (2) within a same molecule:

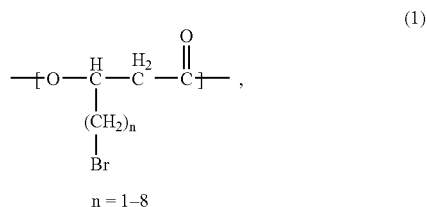

(1)

n = 1–8 wherein n designates a number within a range shown in the chemical formula and can be different from that of another unit in the same molecule;

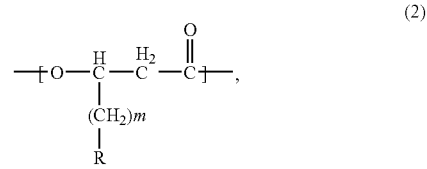

(2)

wherein a pair of R and m is selected from the group consisting of R including a residue having a phenyl structure and m being an integer selected from 1 to 8; R including a residue having a thienyl structure and m being an integer selected from 1 to 8; and R includes a residue having a cyclohexyl structure and m being an integer selected from 0 to 8; and, in case plural units are present, the pair of R and m of one unit can be different from that of another unit in the same molecule.

2. A polyhydroxyalkanoate copolymer according to claim 1, wherein R in the unit represented by the chemical formula (2) is at least one selected from the group consisting of chemical formulas (3) to (14) and, in case plural units are present, can be different from that of another unit in the same molecule:

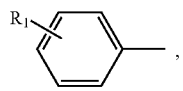
(3)

wherein $R_1$ designates a substituent on the aromatic ring selected from the group consisting of H, a halogen, CN, $NO_2$, $CH_3$, $C_2H_5$, $C_3H_7$, $CF_3$, $C_2F_5$, $C_3F_7$, $CH=CH_2$, and $COOR_2$, wherein $R_2$ is selected from the group consisting of H, Na and K, and, in case plural units are present, $R_1$ can be different from that of another unit in the same molecule;

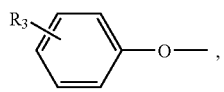
(4)

wherein $R_3$ designates a substituent on the aromatic ring selected from the group consisting of H, a halogen, CN, $NO_2$, $CH_3$, $C_2H_5$, $C_3H_7$, $CF_3$, $C_2F_5$, $C_3F_7$, and $SCH_3$, and, in case plural units are present, $R_3$ can be different from that of another unit in the same molecule;

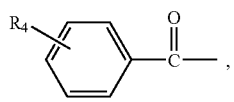
(5)

wherein $R_4$ designates a substituent on the aromatic ring selected from the group consisting of H, a halogen, CN, $NO_2$, $CH_3$, $C_2H_5$, $C_3H_7$, $CF_3$, $C_2F_5$ and $C_3F_7$, and, in case plural units are present, $R_4$ can be different from that of another unit in the same molecule;

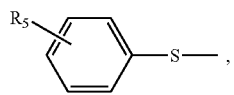
(6)

wherein $R_5$ designates a substituent on the aromatic ring selected from the group consisting of H, a halogen, $CH_3$, $C_2H_5$, $C_3H_7$, $(CH_3)_2$—CH, $(CH_3)_3$—C, CN, $NO_2$, $COOR_6$, and $SO_2R_7$, wherein $R_6$ is selected from the group consisting of H, Na, K, $CH_3$ and $C_2H_5$, and $R_7$ is selected from the group consisting of OH, ONa, OK, a halogen, $OCH_3$ and $OC_2H_5$, and, in case plural units are present, $R_5$ can be different from that of another unit in the same molecule;

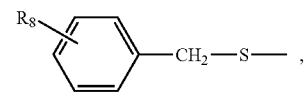
(7)

wherein $R_8$ designates a substituent on the aromatic ring selected from the group consisting of H, a halogen, $CH_3$, $C_2H_5$, $C_3H_7$, $(CH_3)_2$—CH, $(CH_3)_3$—C, CN, $NO_2$, $COOR_9$, and $SO_2R_{10}$, wherein $R_9$ is selected from the group consisting of H, Na, K, $CH_3$ and $C_2H_5$, and $R_{10}$ is selected from the group consisting of OH, ONa, OK, a halogen, $OCH_3$ and $OC_2H_5$, and, in case plural units are present, $R_8$ can be different from that of another unit in the same molecule;

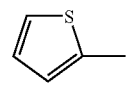
(8)

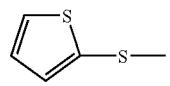
(9)

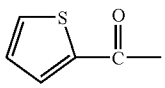
(10)

(11)

wherein $R_{11}$ designates a substituent on the cyclohexyl group selected from the group consisting of H, CN, $NO_2$, a halogen, $CH_3$, $C_2H_5$, $C_3H_7$, $CF_3$, $C_2F_5$, and $C_3F_7$, and, in case plural units are present, $R_{11}$ can be different from that of another unit in the same molecule;

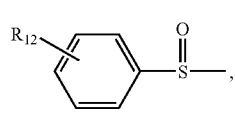
(12)

wherein $R_{12}$ designates a substituent on the aromatic ring selected from the group consisting of H, a halogen, $CH_3$, $C_2H_5$, $C_3H_7$, $(CH_3)_2$—CH, $(CH_3)_3$—C, CN, $NO_2$, $COOR_{13}$, and $SO_2R_{14}$, wherein $R_{13}$ is selected from the group consisting of H, Na, K, $CH_3$ and $C_2H_5$, and $R_{14}$ is selected from the group consisting of OH, ONa, OK, a halogen, $OCH_3$ and $OC_2H_5$, and, in case plural units are present, $R_{12}$ can be different from that of another unit in the same molecule;

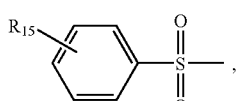
(13)

wherein $R_{15}$ designates a substituent on the aromatic ring selected from the group consisting of H, a halogen, $CH_3$, $C_2H_5$, $C_3H_7$, $(CH_3)_2$—CH, $(CH_3)_3$—C, CN, $NO_2$, $COOR_{16}$, and $SO_2R_{17}$, wherein $R_{16}$ is selected from the group consisting of H, Na, K, $CH_3$ and $C_2H_5$, and $R_{17}$ is selected from the group consisting of OH, ONa, OK, a halogen, $OCH_3$ and $OC_2H_5$, and, in case plural units are present, $R_{15}$ can be different from that of another unit in the same molecule;

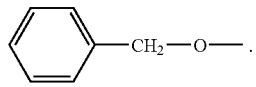

(14)

3. A polyhydroxyalkanoate copolymer according to claim 1, wherein the 3-hydroxy-ω-bromoalkanoic acid unit represented by said chemical formula (1) is at least a 3-hydroxy-8-bromooctanoic acid unit represented by a chemical formula (15) or a 3-hydroxy-6-bromohexanoic acid unit represented by a chemical formula (16), and, in case plural units are present, the 3-hydroxy-ω-bromoalkanoic acid unit can be different from that of another unit in the same molecule:

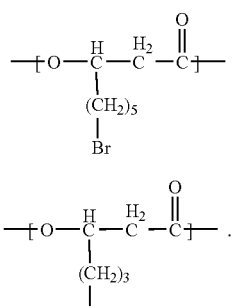

(15)

(16)

4. A polyhydroxyalkanoate copolymer according to claim 1, wherein the 3-hydroxy-ω-bromoalkanoic acid unit represented by said chemical formula (1) is at least one of a 3-hydroxy-11-bromoundecanoic acid unit represented by a chemical formula (17), a 3-hydroxy-9-bromoundecanoic acid unit represented by a chemical formula (18) and a 3-hydroxy-7-bromoheptanoic acid unit represented by a chemical formula (19), and, in case plural units are present, the 3-hydroxy-ω-bromoalkanoic acid unit can be different from that of another unit in the same molecule:

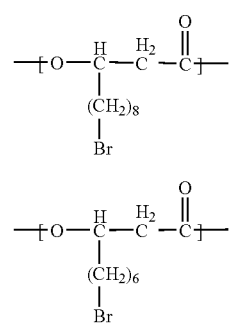

(17)

(18)

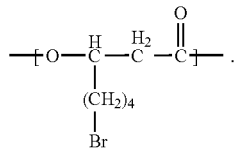

(19)

5. A polyhydroxyalkanoate copolymer according to claim 1, wherein a number-average molecular weight is within a range from 2,000 to 500,000.

6. A method for producing a polyhydroxyalkanoate copolymer including at least a 3-hydroxy-ω-bromoalkanoic acid unit represented by the chemical formula (1) and at least a unit represented by the chemical formula (2) within a same molecule, comprising the step of executing a biosynthesis by a microorganism capable of producing a polyhydroxyalkanoate copolymer including at least the 3-hydroxy-ω-bromoalkanoic acid unit represented by the chemical formula (1) and at least the unit represented by the chemical formula (2) within the same molecule, wherein at least a ω-bromoalkanoic acid represented by a chemical formula (20) and at a compound represented by a chemical formula (21) are utilized as raw materials:

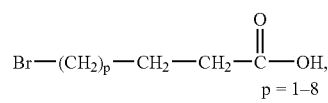

(20)

wherein p is an integer selected within a range indicated in the chemical formula,

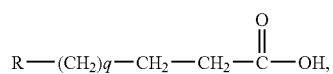

(21)

wherein a pair of R and q is selected from the group consisting of R including a residue having a phenyl structure and q being an integer selected from 1 to 8, R including a residue having a thienyl structure and q being an integer selected from 1 to 8, and R including a residue having a cyclohexyl structure and q being an integer selected from 0 to 8,

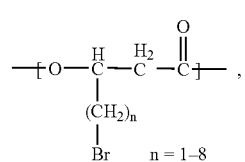

(1)

wherein n designates, independently for each unit, a number within a range shown in the chemical formula, (2)

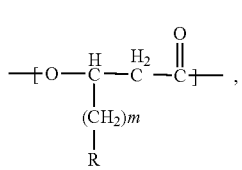

wherein a pair of R and m is selected from the group consisting of R including a residue having a phenyl structure and m being an integer selected from 1 to 8, R including a residue having a thienyl structure and m being an integer selected from 1 to 8, and R includes a residue having a cyclohexyl structure and m being an integer selected from 0 to 8, and, in case plural units are present, the pair of R and m of one unit can be different from that of another unit in the same molecule.

7. A method for producing polyhydroxyalkanoate copolymer according to claim 6, wherein R in the unit represented by said chemical formulas (2) and (21) is at least one selected from the group consisting of the following chemical formulas (3) to (14) and, in case plural units are present, can be different from that of another unit in the same molecule:

(3)

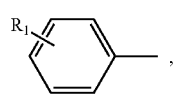

wherein $R_1$ designates a substituent on the aromatic ring selected from the group consisting of H, a halogen, CN, $NO_2$, $CH_3$, $C_2H_5$, $C_3H_7$, $CF_3$, $C_2F_5$, $C_3F_7$, $CH=CH_2$, and $COOR_2$, wherein $R_2$ is selected from the group consisting of H, Na and K, and, in case plural units are present, $R_1$ can be different from that of another unit in the same molecule;

(4)

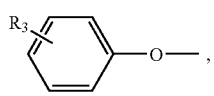

wherein $R_3$ designates a substituent on the aromatic ring selected from the group consisting of H, a halogen, CN, $NO_2$, $CH_3$, $C_2H_5$, $C_3H_7$, $CF_3$, $C_2F_5$, $C_3F_7$, and $SCH_3$, and, in case plural units are present, $R_3$ can be different from that of another unit in the same molecule;

(5)

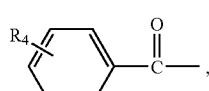

wherein $R_4$ designates a substituent on the aromatic ring selected from the group consisting of H, a halogen, CN, $NO_2$, $CH_3$, $C_2H_5$, $C_3H_7$, $CF_3$, $C_2F_5$ and $C_3F_7$, and, in case plural units are present, $R_4$ can be different from that of another unit in the same molecule;

(6)

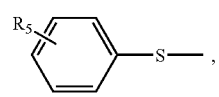

wherein $R_5$ designates a substituent on the aromatic ring selected from the group consisting of H, a halogen, $CH_3$, $C_2H_5$, $C_3H_7$, $(CH_3)_2$—CH, $(CH_3)_3$—C, CN, $NO_2$, $COOR_6$, and $SO_2R_7$, wherein $R_6$ is selected from the group consisting of H, Na, K, $CH_3$ and $C_2H_5$, and $R_7$ is selected from the group consisting of OH, ONa, OK, a halogen, $OCH_3$ and $OC_2H_5$, and, in case plural units are present, $R_5$ can be different from that of another unit in the same molecule;

(7)

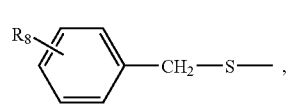

wherein $R_8$ designates a substituent on the aromatic ring selected from the group consisting of H, a halogen, $CH_3$, $C_2H_5$, $C_3H_7$, $(CH_3)_2$—CH, $(CH_3)_3$—C, CN, $NO_2$, $COOR_9$, and $SO_2R_{10}$, wherein $R_9$ is selected from the group consisting of H, Na, K, $CH_3$ and $C_2H_5$, and $R_{10}$ is selected from the group consisting of OH, ONa, OK, a halogen, $OCH_3$ and $OC_2H_5$, and, in case plural units are present, $R_8$ can be different from that of another unit in the same molecule;

(8)

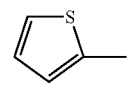

(9)

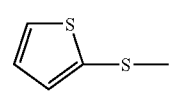

(10)

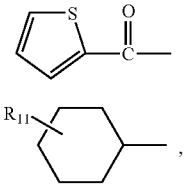

(11)

wherein $R_{11}$ designates a substituent on the cyclohexyl group selected from the group consisting of H, CN, $NO_2$, a halogen, $CH_3$, $C_2H_5$, $C_3H_7$, $CF_3$, $C_2F_5$, and $C_3F_7$, and, in case plural units are present, $R_{11}$ can be different from that of another unit in the same molecule;

(12)

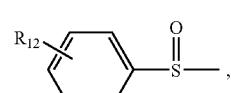

wherein $R_{12}$ designates a substituent on the aromatic ring selected from the group consisting of H, a halogen, $CH_3$, $C_2H_5$, $C_3H_7$, $(CH_3)_2$—CH, $(CH_3)_3$—C, CN, $NO_2$, $COOR_{13}$, and $SO_2R_{14}$, wherein $R_{13}$ is selected from the group consisting of H, Na, K, $CH_3$ and $C_2H_5$, and $R_{14}$ is selected from the group consisting of OH, ONa, OK, a halogen, $OCH_3$ and $OC_2H_5$, and, in case plural units are present, $R_{12}$ can be different from that of another unit in the same molecule;

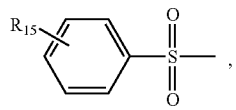
(13)

wherein $R_{15}$ designates a substituent on the aromatic ring selected from the group consisting of H, a halogen, $CH_3$, $C_2H_5$, $C_3H_7$, $(CH_3)_2$—CH, $(CH_3)_3$—C, CN, $NO_2$, $COOR_{16}$, and $SO_2R_{17}$, wherein $R_{16}$ is selected from the group consisting of H, Na, K, $CH_3$ and $C_2H_5$, and $R_{17}$ is selected from the group consisting of OH, ONa, OK, a halogen, $OCH_3$ and $OC_2H_5$, and, in case plural units are present, $R_{15}$ can be different from that of another unit in the same molecule;

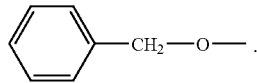
(14)

8. A method for producing a polyhydroxyalkanoate copolymer according to claim 6, comprising culturing said microorganisms in a culture medium including at least the ω-bromoalkanoic acid represented by said chemical formula (20) and at least the compound represented by said chemical formula (21).

9. A method for producing a polyhydroxyalkanoate copolymer according to claim 8, wherein said culture medium includes a peptide.

10. A method for producing a polyhydroxyalkanoate copolymer according to claim 9, wherein said peptide is a polypeptone.

11. A method for producing a polyhydroxyalkanoate copolymer according to claim 8, wherein said culture medium includes a yeast extract.

12. A method for producing a polyhydroxyalkanoate copolymer according to claim 8, wherein said culture medium includes an organic acid or a salt thereof.

13. A method for producing a polyhydroxyalkanoate copolymer according to claim 8, wherein said culture medium includes an amino acid or a salt thereof.

14. A method for producing a polyhydroxyalkanoate copolymer according to claim 8, wherein said culture medium includes a sugar.

15. A method for producing a polyhydroxyalkanoate copolymer according to claim 8, wherein said culture medium includes a straight-chain alkanoic acid with 4 to 12 carbon atoms or a salt thereof.

16. A method for producing a polyhydroxyalkanoate copolymer according to claim 8, further comprising the step of recovering from cells of said microorganisms said polyhydroxyalkanoate copolymer including at least the 3-hydroxy-ω-bromoalkanoic acid unit represented by said chemical formula (1) and at least the unit represented by said chemical formula (2) within the same molecule.

* * * * *

UNITED STATES PATENT AND TRADEMARK OFFICE
CERTIFICATE OF CORRECTION

PATENT NO. : 7,135,540 B2
APPLICATION NO. : 10/359600
DATED : November 14, 2006
INVENTOR(S) : Tsutomu Honma et al.

It is certified that error appears in the above-identified patent and that said Letters Patent is hereby corrected as shown below:

ON THE TITLE PAGE ITEM -54-:

Title, "POLYHYDROXYALKANOATE" should read --NOVEL POLYHYDROXYALKANOATE--.

ON THE TITLE PAGE ITEM -56- REFERENCES CITED:

Other Publications:
        After "Y.B. Kim et al.,", "Obtain d" should read --Obtained--;
        After "Helmut Ritter et al.,", "Sid" should read --Side--;
        After "Marieta Constantin et al.,", "Copolym rs" should read --Copolymers--;
        After "Alexander Steinbüchel et al.,", "Polyhydroxyalcanoic" should read --Polyhydroxyalkanoic--;
        After "Richard Ashby et al.,", "Microbal" should read --Microbial--;
        After "Leigh A. Madden et al.," "Involvm nt" should read --Involvement--;
        After "Marianela Andújar et al.,", "Pseudomonal" should read --Pseudomonas--;
        After "Moon Yeun Lee et al.,", "Microbal" should read --Microbial--;
        After "Katsutoshi Hori et al.,", "Pseudomonal" should read --Pseudomonas--;
        After "Yasuo Takagi et al.,", "with a" should read --with--;
        After "Roland G. Lageveen et al.,", "Hydroxyalkenoates,"" should read --Hydroxyalkanoates,"--; and
        After "Roland G. Lageveen et al.,", "Marienela Andújar et al., "Polyesters Produced by Pseudomonal oleovorans Containing Cyclohexyl Groups," 30 Macromol. 1611-1615 (1997)." should be deleted.

COLUMN 1:

Line 1, "POLYHYDROXYALKANOATE" should read --NOVEL POLYHYDROXYALKANOATE--.

COLUMN 2:

Line 22, "stain," should read --strain,--;
    Line 56, "co-existence of" should read --in combination with--;
    Line 60, "acid," should read --acid--; and
    Line 61, "in the coexistence of" should read --using as a raw material--.

UNITED STATES PATENT AND TRADEMARK OFFICE
CERTIFICATE OF CORRECTION

PATENT NO. : 7,135,540 B2
APPLICATION NO. : 10/359600
DATED : November 14, 2006
INVENTOR(S) : Tsutomu Honma et al.

It is certified that error appears in the above-identified patent and that said Letters Patent is hereby corrected as shown below:

COLUMN 3:

Lines 40-46, " 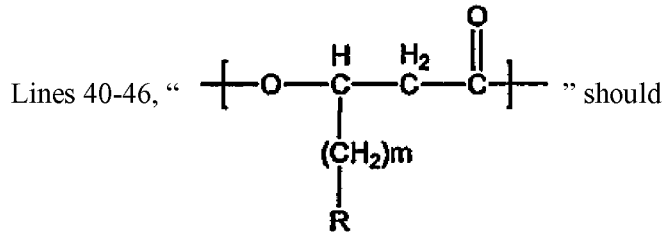 " should read -- 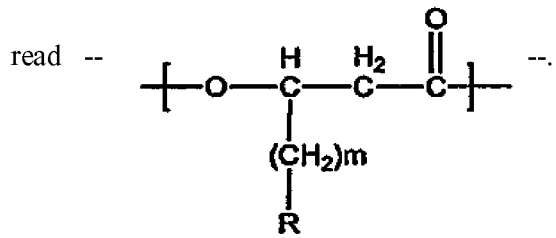 --.

COLUMN 8:

Lines 3-9, " 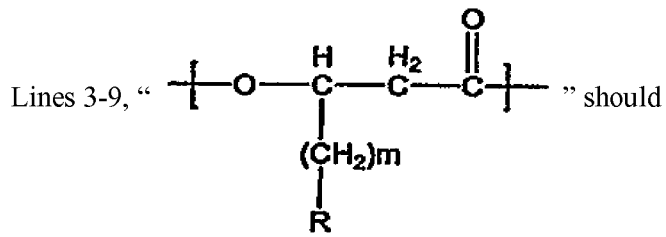 " should read -- 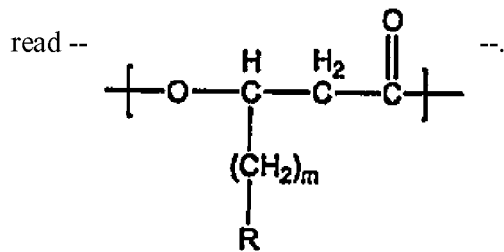 --.

UNITED STATES PATENT AND TRADEMARK OFFICE
CERTIFICATE OF CORRECTION

| | | |
|---|---|---|
| PATENT NO. | : 7,135,540 B2 | |
| APPLICATION NO. | : 10/359600 | |
| DATED | : November 14, 2006 | |
| INVENTOR(S) | : Tsutomu Honma et al. | |

It is certified that error appears in the above-identified patent and that said Letters Patent is hereby corrected as shown below:

COLUMN 13:

Line 45, "preferred" should read --preferred--.

COLUMN 14:

Line 65, "acid," should read --acid),--.

COLUMN 19:

Table 5, "2.12" should read --212--.

COLUMN 38:

Line 32-40, "  " should read --  --.

UNITED STATES PATENT AND TRADEMARK OFFICE
CERTIFICATE OF CORRECTION

PATENT NO. : 7,135,540 B2
APPLICATION NO. : 10/359600
DATED : November 14, 2006
INVENTOR(S) : Tsutomu Honma et al.

It is certified that error appears in the above-identified patent and that said Letters Patent is hereby corrected as shown below:

COLUMN 43:

Line 32-40, " 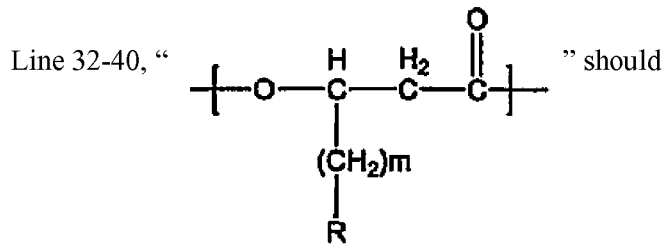 " should read -- 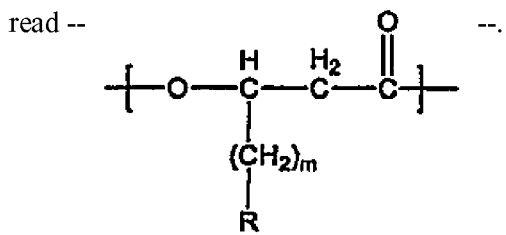 --.

Signed and Sealed this

Eighth Day of May, 2007

JON W. DUDAS
*Director of the United States Patent and Trademark Office*